United States Patent [19]
Backhaus et al.

[11] Patent Number: 5,633,433
[45] Date of Patent: May 27, 1997

[54] RUBBER PARTICLE PROTEIN GENE FROM GUAYULE

[75] Inventors: Ralph A. Backhaus, Mesa; Zhiqiang Pan, Tempe, both of Ariz.

[73] Assignee: Arizona Board of Regents, a body corporate of the State of Arizona, acting for and on behalf of Arizona State University, Tempe, Ariz.

[21] Appl. No.: 240,012

[22] Filed: May 9, 1994

Related U.S. Application Data

[63] Continuation of Ser. No. 872, Jan. 5, 1993, abandoned, which is a continuation-in-part of Ser. No. 687,456, Apr. 17, 1991, abandoned.

[51] Int. Cl.$^6$ .......................... C12N 15/29; C12N 15/63; A01H 1/00; A01H 5/00
[52] U.S. Cl. .................. 800/205; 435/172.3; 435/320.1; 536/23.6; 800/DIG. 9
[58] Field of Search ...................... 435/69.1, 172.1, 435/172.3, 193, 320.1; 536/27, 23.6; 800/200, 205, 250, DIG. 69, DIG. 43; 935/10

[56] References Cited

U.S. PATENT DOCUMENTS 4,983,729  1/1991  Sikora ........................................ 536/28

OTHER PUBLICATIONS

Benedict et al. 1990, Plant Physiol. 92:816–821.

Weising et al. 1988. Annu. Rev. Genet, 22:421–477.

Backhaus et al. 1989. Journal of Cellular Biochemistry. Supp. 130. Miol. p. 252.

Backhaus et al. 1986. In Biochemistry And Regulation of CIS Polyisoprene in Plants, NSF Sponsored Workshop Pub. Benedict, ed. pp. 204–220.

*Primary Examiner*—Erich E. Veitenheimer
*Attorney, Agent, or Firm*—Brumbaugh, Graves, Donohue & Raymond

[57] ABSTRACT

Guayule rubber particles, contain several characteristic proteins. The most abundant of these proteins, the rubber particle protein (RPP) has been shown to be a non-monooxygenase, cytochrome P450, heme-binding protein that is necessary for rubber biosynthesis. A full-length cDNA clone for guayule RPP has been isolated, sequenced and characterized. The pRPP30 coding sequence is transferable to other prokaryotic or eukaryotic host organisms wherein the RPP DNA will be expressed to produce functional RPP for rubber biosynthesis.

21 Claims, 21 Drawing Sheets

CNBr #1

Pro-Leu-Thr-Lys-Ser-Val-Val-Tyr-Glu-Ser-Leu-Arg-Ile-Glu-Pro-Pro-Val

CNBr #2

Met-Glu-Gln-Ala-Glu-Lys-Leu-Gly-Val-Pro-Lys-Asp-Glu-Ala-Val-His-Asn-Ile-Leu-Phe-Ala-Val-Cys-Phe-Asn-Thr-Phe-Gly-Gly-Val-Lys

CNBr #3

Leu-Phe-Gly-Tyr-Gln-Pro-Phe-Ala-Thr-Lys-Asp-Pro-Lys-Val-Phe-Asp-Arg-Pro-Glu-Gly-Phe-Val-Pro-Asp-Arg-Phe-Val-Gly-Asp-Gly-Glu-Ala-Leu-Leu-Lys-Tyr

CNBr #4

Leu-Lys-Asn-Ser-Ser-Asn-Arg-Val-Ile-Pro-Gln-Phe-Glu-Thr-Thr-Tyr-Tyr-Glu-Leu-Phe-Glu-Gly-Leu-Glu-Ala

FIG. 1

Sequence P5:      Phe Gly Tyr Gln Pro Phe Ala    (sense)
20-mer            TTY GGN TAY CAR CYN TTY GC Sequence P6:      GC YTC NCC RTC NCC NAC RAA     (antisense)
20-mer Sequence P1:      Ile Pro Gln Phe Glu Thr        (sense)
17-mer            ATH CYN CAR TTY GAR AC Sequence P9:      TT NAC NCC NCC RAA NGT RTT TAA (antisense)
23-mer Sequence P8:      Met Glu Gln Ala Glu Lys Leu    (sense)
20-mer            ATG GAR CAR GCN GAR AAR YT Sequence P3:      GT YTC RAA YTG NRG DAT         (antisense)
17-mer

FIG. 2A

Sequence P5/6: A PCR amplified 92 bp cDNA sequence for an RPP sequence between P5 and P6 of CNBr fragment #3.

```
92-mer     TTC GGG TAC CAA CCG TTT GCA ACC AAG GAC CCG AAA
           GTA TTT GAC CGA CCT GAG GAG TTT GTC CCT GAT CGG
           TTC GTT GGG GAT GGC GAG GC
```

Sequence P5, P6 and P5/6 code for DNA contained within CNBr fragment #3; sequences P1 and P3 code for DNA contained in CNBr fragment #4; sequence P8 and P9 code for DNA contained in CNBr fragment #2.

Coding redundancies are:

| | | |
|---|---|---|
| N = C, T, A or C | H = A, C or T | S = G or C |
| R = A or G | B = C, G or T | K = G or T |
| Y = C or T | V = A, C or G | W = A or T |
| M = A or C | D = A, G or T | |

FIG. 2B

CTCACATTCAAAACAGTCAAAAC ATG GAC CCA TCG TCT AAA CCC CTC CGT    50
                        Met Asp Pro Ser Ser Lys Pro Leu Arg
                         1                5

GAA ATC CCC GGC TCT TAT GGC ATT CCT TTC TTT CAA CCG ATA AAA    95
Glu Ile Pro Gly Ser Tyr Gly Ile Pro Phe Phe Gln Pro Ile Lys
 10              15              20

GAC CGG TTG GAG TAT TTT TAC GGG ACC GGA GGT CGA GAC GAG TAC   140
Asp Arg Leu Glu Tyr Phe Tyr Gly Thr Gly Gly Arg Asp Glu Tyr
 25              30              35

TTC CGG TCC CGC ATG CAA AAA TAC CAA TCC ACG GTA TTT CGA GCC   185
Phe Arg Ser Arg Met Gln Lys Tyr Gln Ser Thr Val Phe Arg Ala
 40              45              50

AAC ATG CCA CCG GGC CCT TTC GTA AGC AGC AAC CCG AAG GTA ATC   230
Asn Met Pro Pro Gly Pro Phe Val Ser Ser Asn Pro Lys Val Ile
 55              60              65

GTC CTA CTC GAC GCC AAA AGC TTT CCG ATA CTC TTT GAT GTA TCC   275
Val Leu Leu Asp Ala Lys Ser Phe Pro Ile Leu Phe Asp Val Ser
 70              75              80

FIG. 3A

```
AAA GTC GAG AAG AAA GAT TTG TTC ACC GGA ACT TAC ATG CCG TCA         320
Lys Val Glu Lys Lys Asp Leu Phe Thr Gly Thr Tyr Met Pro Ser
85                      90                  95

ACC AAA CTC ACT GGC GCG TAT CGC GTA CTC TCG TAC CTC GAC CCA         365
Thr Lys Leu Thr Gly Ala Tyr Arg Val Leu Ser Tyr Leu Asp Pro
100                     105                 110

TCC GAA CCT AGA CAT GCT CAA CTT AAG AAC CTC TTG TTC TTC ATG         410
Ser Glu Pro Arg His Ala Gln Leu Lys Asn Leu Leu Phe Phe Met
115                     120                 125
                                                      Primer P1
                                                      --- --- --- -->
CTT AAA AAT TCA AGC AAC CGA GTC ATC CCA CAG TTT GAA ACC ACT         455
Leu Lys Asn Ser Ser Asn Arg Val Ile Pro Gln Phe Glu Thr Thr
130                     135                 140
 *   *   *              *    *   *    *    *   *   *   *   *
 (CNBr #4)                       <--- --- --- Primer P3

TAC ACC GAA CTC TTT GAA GGT CTT GAA GCC GAG CTA GCC AAA AAC         500
Tyr Thr Glu Leu Phe Glu Gly Leu Glu Ala Glu Leu Ala Lys Asn
145                     150                 155
 *   *   *    *   *   *   *   *   *    *    *

FIG. 3B
```

```
GGG AAA GCC GCG TTC AAC GAT GTT GGT GAA CAA GCG GCT TTC CGG    545
Gly Lys Ala Ala Phe Asn Asp Val Gly Glu Gln Ala Ala Phe Arg
160                           165                 170

TTT TTG GGC AGG GCT TAT TTT AAC TCG AAC CCG GAA GAA ACC AAA    590
Phe Leu Gly Arg Ala Tyr Phe Asn Ser Asn Pro Glu Glu Thr Lys
175                           180                 185

CTA GGA ACT AGT GCG CCT ACG TTA ATT AGC TCG TGG GTG TTA TTT    635
Leu Gly Thr Ser Ala Pro Thr Leu Ile Ser Ser Trp Val Leu Phe
190                           195                 200

AAT CTT GCC CCC ACG CTC GAC CTT GGA CTG CCG TTC TTG CAG        680
Asn Leu Ala Pro Thr Leu Asp Leu Gly Leu Pro Phe Leu Gln
205                           210                 215

GAA CCT CTT CTA CAC ACT TTC CGA CTG CCG GCG TTC CTG ATT AAG    725
Glu Pro Leu Leu His Thr Phe Arg Leu Pro Ala Phe Leu Ile Lys
220                           225                 230

AGT ACT TAC AAC AAA CTT TAC GAT TAT TTC CAG TCG GTT GCG ACT    770
Ser Thr Tyr Asn Lys Leu Tyr Asp Tyr Phe Gln Ser Val Ala Thr
235                           240                 245
```

FIG. 3C

```
         Primer P8
         ---  ---  ---  --->
CCG GTT ATG GAA CAA GCA GAA AAA TTA GGG GTT CCG AAG GAT GAA       815
Pro Val Met Glu Gln Ala Glu Lys Leu Gly Val Pro Lys Asp Glu
250             255                 260
 *   *   *                                   *   *   *
        (CNBr #2)

GCT GTG CAC AAT ATC TTA TTC GCG GTT TGC TTC AAT ACT TTT GGT       860
Ala Val His Asn Ile Leu Phe Ala Val Cys Phe Asn Thr Phe Gly
265             270                 275
 *   *                                       *   *   *   ---  ---  ---
                                                         <---  ---  ---
                                                         Primer P9

GGT GTT AAG ATC CTC TTC CCG AAT ACA CTC AAA TGG ATC GGA GTT       905
Gly Val Lys Ile Leu Phe Pro Asn Thr Leu Lys Trp Ile Gly Val
280             285                 290
 *   *           *
 ---  ---

GCT GGT GAG AAT TTG CAT ACC CAA TTG GCG GAA GAG ATT AGA GGT       950
Ala Gly Glu Asn Leu His Thr Gln Leu Ala Glu Glu Ile Arg Gly
295             300                 305

GCT ATA AAA TCA TAC GGG GAC GGT AAC GTG ACG CTG GAA GCA ATC       995
Ala Ile Lys Ser Tyr Gly Asp Gly Asn Val Thr Leu Glu Ala Ile
310             315                 320
```

FIG. 3D

```
GAG CAG ATG CCG TTG ACG AAG TCA GTG GTG TAC GAG TCC CTC AGG      1040
Glu Gln Met Pro Leu Thr Lys Ser Val Val Tyr Glu Ser Leu Arg
325                     330                     335
 *   *   *   *   *   *   *   *   *   *   *   *   *   *   *
        (CNBr #1)

ATT GAA CCA CCA GTG CCT CCG CAA TAT GGA AAA GCC AAA AGC AAC      1085
Ile Glu Pro Pro Val Pro Pro Gln Tyr Gly Lys Ala Lys Ser Asn
340                     345                     350
 *   *   *   *   *   *   *   *   *   *   *   *   *   *   *

TTT ACC ATA GAG TCA CAC GAC GCC ACT TTC GAA GTC AAA AAA GGA      1130
Phe Thr Ile Glu Ser His Asp Ala Thr Phe Glu Val Lys Lys Gly
355                     360                     365
                        Primer P5
                        --- --- --- --- -->
 *   *   *   *   *   *   *   *   *   *   *   *   *   *   *

GAA ATG TTA TTC GGG TAC CAA CCG TTT GCA ACC AAG GAC CCG AAA      1175
Glu Met Leu Phe Gly Tyr Gln Pro Phe Ala Thr Lys Asp Pro Lys
370                     375                     380
 *   *   *   *   *   *   *   *   *   *   *   *   *   *   *
        (CNBr #3)
```

FIG. 3E

```
GTA TTT GAC CGA CCT GAG GAG TTT GTC CCT GAT CGG TTC GTT GGG    1220
Val Phe Asp Arg Pro Glu Glu Phe Val Pro Asp Arg Phe Val Gly
385              390              395              
 *   *   *   *   *   *   *   *   *   *   *   *   *  <--
                                                     ---
                                                     ---
GAT GGC GAG GCA TTG TTG AAG TAC GTA TGG TCT AAT GGG CCG         1265
Asp Gly Glu Ala Leu Leu Lys Tyr Val Trp Ser Asn Gly Pro
400              405              410              
 *   *   *   *   *   *   *
---
---
---
Primer P6

GAG ACA GAG AGT CCG ACA GTT GAA AAT AAA CAA TGT GCC GGA AAA    1310
Glu Thr Glu Ser Pro Thr Val Glu Asn Lys Gln Cys Ala Gly Lys
415              420              425

GAC TTT GTC GTG CTG ATA ACG AGG TTG TTT GTC ATT GAA CTT TTC    1355
Asp Phe Val Val Leu Ile Thr Arg Leu Phe Val Ile Glu Leu Phe
430              435              440

CGG CGA TAT GAC TCT TTT GAA ATC GAA TTA GGC GAG TCT CCT TTG    1400
Arg Arg Tyr Asp Ser Phe Glu Ile Glu Leu Gly Glu Ser Pro Leu
445              450              455              
```

FIG. 3F

```
GGT GCA GCT GTC ACA CTT ACG TTC CTG AAG AGA GCT AGT ATA TGA       1445
Gly Ala Ala Val Thr Leu Thr Phe Leu Lys Arg Ala Ser Ile
460                     465                     470

TTGCAGCCAT AACTAGTTAC CCTGTACTAG CACGTTAGTA AAATGATGTT            1495

TGATATGTTT TTCAAGTAAA TATAAAAATA AAGTAATAAA AAAGGGATGT            1545

GTATATGGGG AGGGGTGTGG GAGGTCAGGA TCAAGTATGT ATCAAGGTTG            1595

TTTGTATTAT TCGTGCTATG AATAAGTGTT GAATTTGCAG TTCAAGAGCA            1645

TAAAATAAAT ATTGTTTCAC AAAATTTAGA AAAAAAAAAA AAAAAAA               1692
```

FIG. 3G

```
AOS  51 PIKIPGITSQPPPSSDETTLPIRQIPGDYGLPGIGPIQDRLDYFYN.QGR  99
         |... |:|:|||.||:| :.||.|||:|||. .||
RPP   1 ..............MDPSSKPLREIPGSYGIPFFQPIKDRLEYFYGTGGR  36

AOS 100 EEFFKSRLQKYKSTVYRANMPPGPFIASNPRVIVLLDAKSFPVLFDMSKV 149
         :|:|:||:|||.|||:|||||||||:..|||:||||||||||:|||:|||
RPP  37 DEYFRSRMQKYQSTVFRANMPGPFVSSNPKVIVLLDAKSFPILFDVSKV  86

AOS 150 EKKDLFTGTYMPSTELTGGYRILSYLDPSEPNHTKLKQLLFNLIKNRRDY 199
         |||||||||||||.|||:||:||||||||.|..||.||| ::||..:
RPP  87 EKKDLFTGTYMPSTKLTGAYRVLSYLDPSEPRHAQLKNLLFFMLKNSSNR 136

AOS 200 VIPEFSSSFTDLCEVVEYDLATKGKAAFNDPAEQAAFNFLSRAFFGVKPI 249
         |||:|...:|:| |.:| :||..||||||||.:|||||.||:||:|. .|
RPP 137 VIPQFETTYTELFEGLEAELAKNGKAAFNDVGEQAAFRFLGRAYFNSNPE 186

AOS 250 DTPLGKDAPSLISKWVLFNLAPILSVGLPKEVEEATLHSVRLPPLLVQND 299
         :|.||..||.|||.||||||||.|.:|||. ::|: ||..|||:::...
RPP 187 ETKLGTSAPTLISSWVLFNLAPTLDLGLPWFLQEPLLHTFRLPAFLIKST 236

AOS 300 YHRLYEFFTSAAGSVLDEAEQSGISRDEACHNILFAVCFNSWGGFKILFP 349
         |::||::| |.|...|:::||. |.:::|||.|||||||||.:||.|||||
RPP 237 YNKLYDYFQSVATPVMEQAEKLGVPKDEAVHNILFAVCFNTFGGVKILFP 286

AOS 350 SLMKWIGRAGLELHTKLAQEIRSAIQSTGGGKVTMAAMEQMPLMKSVVYE 399
         . :|||| ||  :|||.||:|||:||.| |:|.||..|:||||| ||||||
RPP 287 NTLKWIGVAGENLHTQLAEEIRGAIKSYGDGNVTLEAIEQMPLTKSVVYE 336

AOS 400 TLRIEPPVALQYGKAKKDFILESHEAAYQVKEGEMLFGYQPFATKDPKIF 449
         .|||||||: ||||||..:|.:|||:|.:::||.||||||||||||||||:|
RPP 337 SLRIEPPVPPQYGKAKSNFTIESHDATFEVKKGEMLFGYQPFATKDPKVF 386

AOS 450 DRPEEFVADRFVGEGVKLMEYVMWSNGPETETPSVANKQCAGKDFVVMAA 499
         |||||||:|||||:| |:.|| ||||||||.|.|.|||||||||||||: .
RPP 387 DRPEEFVPDRFVGDGEALLKYVWWSNGPETESPTVENKQCAGKDFVVLIT 436

AOS 500 RLFVVELFKRYDSFDIEVGTSSLGASITLTSLKRSTF 536
         ||||:|||:|||||:|.|.|||.:|||  |||...:
RPP 437 RLFVIELFRRYDSFEIELGESPLGAAVTLTFLKRASI 473
```

FIG. 5

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 17 amino acid residues
        ( B ) TYPE: amino acid
        ( D ) TOPOLOGY: linear ( i i ) MOLECULE TYPE:
        ( A ) DESCRIPTION: CNBr peptide #1 of guayule RPP ( i i i ) HYPOTHETICAL: no ( i v ) ANTI-SENSE: no ( v ) FRAGMENT TYPE: internal fragment ( v i ) ORIGINAL SOURCE:
        ( A ) ORGANISM: Parthenium argentatum
        ( B ) STRAIN: 11591
        ( D ) DEVELOPMENTAL STAGE: cortex from secondary
            growth of stems
        ( F ) TISSUE TYPE: Stembark ( i x ) FEATURE:
        ( A ) NAME/KEY: CNBr #1 of guayule RPP
        ( B ) LOCATION: internal region of RPP
        ( C ) IDENTIFICATION METHOD: by experiment using
            an amino acid sequenator
        ( C ) OTHER INFORMATION: RPP is the rubber particle
            protein bound to natural rubber and is
            essential for rubber formation in guayule.

( x i ) SEQUENCE DESCRIPTION: SEQ ID NO: 1:

Pro Leu Thr Lys Ser Val Val Tyr Glu Ser Leu Arg Ile Glu Pro Pro Val
            5                        1 0                   1 5

( 2 ) INFORMATION FOR SEQ ID NO: 2:

( i ) SEQUENCE CHARACTERISTICS:
        ( A ) LENGTH: 31 amino acid residues
        ( B ) TYPE: amino acid
        ( D ) TOPOLOGY: linear ( i i ) MOLECULE TYPE:
        ( A ) DESCRIPTION: CNBr peptide #2 of guayule RPP ( i i i ) HYPOTHETICAL: no ( i v ) ANTI-SENSE: no ( v ) FRAGMENT TYPE: internal fragment ( v i ) ORIGINAL SOURCE:
        ( A ) ORGANISM: Parthenium argentatum
        ( B ) STRAIN: 11591
        ( D ) DEVELOPMENTAL STAGE: cortex from secondary
            growth of stems
        ( F ) TISSUE TYPE: Stembark ( i x ) FEATURE:

(A) NAME/KEY: CNBr #2 of guayule RPP
(B) LOCATION: internal region of RPP
(C) IDENTIFICATION METHOD: by experiment using
    an amino acid sequenator
(C) OTHER INFORMATION: RPP is the rubber particle
    protein bound to natural rubber and is
    essential for rubber formation in guayule.

(x i) SEQUENCE DESCRIPTION: SEQ ID NO: 2:

```
Met Glu Gln Ala Glu Lys Leu Gly Val Pro Lys Asp Glu Ala Val
                  5                  10                  15

His Asn Ile Leu Phe Ala Val Cys Phe Asn Thr Phe Gly Gly Val Lys
                 20                  25                  30
```

(2) INFORMATION FOR SEQ ID NO: 3:

(i) SEQUENCE CHARACTERISTICS:
       (A) LENGTH: 36 amino acid residues
       (B) TYPE: amino acid
       (D) TOPOLOGY: linear (i i) MOLECULE TYPE:
       (A) DESCRIPTION: CNBr peptide #3 of guayule RPP (i i i) HYPOTHETICAL: no (i v) ANTI-SENSE: no (v) FRAGMENT TYPE: internal fragment (v i) ORIGINAL SOURCE:
       (A) ORGANISM: Parthenium argentatum
       (B) STRAIN: 11591
       (D) DEVELOPMENTAL STAGE: cortex from secondary
           growth of stems
       (F) TISSUE TYPE: Stembark (i x) FEATURE:
       (A) NAME/KEY: CNBr #3 of guayule RPP
       (B) LOCATION: internal region of RPP
       (C) IDENTIFICATION METHOD: by experiment using
           an amino acid sequenator
       (C) OTHER INFORMATION: RPP is the rubber particle
           protein bound to natural rubber and is
           essential for rubber formation in guayule.

(x i) SEQUENCE DESCRIPTION: SEQ ID NO: 3:

```
Leu Phe Gly Tyr Gln Pro Phe Ala Thr Lys Asp Pro Lys Val Phe
                 5                  10                  15

Asp Arg Pro Glu Glu Phe Val Pro Asp Arg Phe Val Gly Asp Gly
                20                  25                  30

Glu Ala Leu Leu Lys Tyr
                35
```

(2) INFORMATION FOR SEQ ID NO: 4:

(i) SEQUENCE CHARACTERISTICS:
       (A) LENGTH: 25 amino acid residues
       (B) TYPE: amino acid
       (D) TOPOLOGY: linear (i i) MOLECULE TYPE:
       (A) DESCRIPTION: CNBr peptide #4 of guayule RPP (i i i) HYPOTHETICAL: no (i v) ANTI-SENSE: no (v) FRAGMENT TYPE: internal fragment (v i) ORIGINAL SOURCE:
       (A) ORGANISM: Parthenium argentatum
       (B) STRAIN: 11591

(D) DEVELOPMENTAL STAGE: cortex from secondary
growth of stems
(F) TISSUE TYPE: Stembark (ix) FEATURE:
(A) NAME/KEY: CNBr #4 of guayule RPP
(B) LOCATION: internal region of RPP
(C) IDENTIFICATION METHOD: by experiment using
an amino acid sequenator
(D) OTHER INFORMATION: RPP is the rubber particle
protein bound to natural rubber and is
essential for rubber formation in guayule.

(xi) SEQUENCE DESCRIPTION: SEQ ID NO: 4:

Leu Lys Asn Ser Ser Asn Arg Val Ile Pro Gln Phe Glu Thr Thr
                    5                   10                  15

Tyr Tyr Glu Leu Phe Glu Gly Leu Glu Ala
                20                  25

(2) INFORMATION FOR SEQ ID NO: 5:

(i) SEQUENCE CHARACTERISTICS:
(A) LENGTH: 20 bases
(B) TYPE: nucleic acid
(C) STRANDEDNESS: single
(D) TOPOLOGY: linear (ii) MOLECULE TYPE:
(A) DESCRIPTION: Oligonucleotide sequence deduced
from RPP amino acid sequence (iii) HYPOTHETICAL: no (iv) ANTI-SENSE: no (vi) ORIGINAL SOURCE:
(A) ORGANISM: Parthenium argentatum
(B) STRAIN: 11591
(D) DEVELOPMENTAL STAGE: cortex from secondary
growth of stems
(F) TISSUE TYPE: Stembark (ix) FEATURE:
(A) NAME/KEY: P5 primer, sense strand for CNBr
peptide #3 (SEQ. ID No. 3)
(D) OTHER INFORMATION: RPP is the rubber particle
protein bound to natural rubber in guayule and
is essential for rubber formation in guayule (xi) SEQUENCE DESCRIPTION: SEQ ID NO: 5:

TT Y  GGN  TA Y  CAR  C Y N  TT Y  GC      20
Phe  Gly  Tyr  Gln  Pro  Phe  Ala
                      5

(2) INFORMATION FOR SEQ ID NO: 6:

(i) SEQUENCE CHARACTERISTICS:
(A) LENGTH: 20 bases
(B) TYPE: nucleic acid
(C) STRANDEDNESS: single
(D) TOPOLOGY: linear (ii) MOLECULE TYPE:
(A) DESCRIPTION: Oligonucleotide sequence deduced
from RPP amino acid sequence (iii) HYPOTHETICAL: no (iv) ANTI-SENSE: no (vi) ORIGINAL SOURCE:
(A) ORGANISM: Parthenium argentatum
(B) STRAIN: 11591
(D) DEVELOPMENTAL STAGE: cortex from secondary
growth of stems (F) TISSUE TYPE: Stembark (ix) FEATURE:
  (A) NAME/KEY: P6 primer, sense strand for CNBr peptide #3 (SEQ ID No. 3)
  (D) OTHER INFORMATION: RPP is the rubber particle protein bound to natural rubber in guayule and is essential for rubber formation in guayule (xi) SEQUENCE DESCRIPTION: SEQ ID NO: 6:

GCY TCNCCRT CNCCNACRAA    20

(2) INFORMATION FOR SEQ ID NO: 7:

(i) SEQUENCE CHARACTERISTICS:
    (A) LENGTH: 17 bases
    (B) TYPE: nucleic acid
    (C) STRANDEDNESS: single
    (D) TOPOLOGY: linear (ii) MOLECULE TYPE:
    (A) DESCRIPTION: Oligonucleotide sequence deduced from RPP amino acid sequence (iii) HYPOTHETICAL: no (iv) ANTI-SENSE: no (vi) ORIGINAL SOURCE:
    (A) ORGANISM: Parthenium argentatum
    (B) STRAIN: 11591
    (D) DEVELOPMENTAL STAGE: cortex from secondary growth of stems
    (F) TISSUE TYPE: Stembark (ix) FEATURE:
    (A) NAME/KEY: P1 primer, sense strand for CNBr peptide #4 (SEQ. ID No. 4)
    (D) OTHER INFORMATION: RPP is the rubber particle protein bound to natural rubber in guayule and is essential for rubber formation in guayule (xi) SEQUENCE DESCRIPTION: SEQ ID NO: 7:

ATH CYN CAR TTY GAR AC    17
Ile Pro Gln Phe Glu Thr
              5

(2) INFORMATION FOR SEQ ID NO: 8:

(i) SEQUENCE CHARACTERISTICS:
    (A) LENGTH: 23 bases
    (B) TYPE: nucleic acid
    (C) STRANDEDNESS: single
    (D) TOPOLOGY: linear (ii) MOLECULE TYPE:
    (A) DESCRIPTION: Oligonucleotide sequence deduced from RPP amino acid sequence (iii) HYPOTHETICAL: no (iv) ANTI-SENSE: no (vi) ORIGINAL SOURCE:
    (A) ORGANISM: Parthenium argentatum
    (B) STRAIN: 11591
    (D) DEVELOPMENTAL STAGE: cortex from secondary growth of stems
    (F) TISSUE TYPE: Stembark (ix) FEATURE:
    (A) NAME/KEY: P9 primer, anti-sense strand for CNBr peptide #2 (SEQ. ID No. 2)
    (D) OTHER INFORMATION: RPP is the rubber particle protein bound to natural rubber in guayule and is essential for rubber formation in guayule ( x i ) SEQUENCE DESCRIPTION: SEQ ID NO: 8:

TTNACNCCNC CRAANGTRTT TAA    23

( 2 ) INFORMATION FOR SEQ ID NO: 9:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE:
        ( A ) DESCRIPTION: Oligonucleotide sequence deduced
            from RPP amino acid sequence ( i i i ) HYPOTHETICAL: no ( i v ) ANTI-SENSE: no ( v i ) ORIGINAL SOURCE:
        ( A ) ORGANISM: Parthenium argentatum
        ( B ) STRAIN: 11591
        ( D ) DEVELOPMENTAL STAGE: cortex from secondary
            growth of stems
        ( F ) TISSUE TYPE: Stembark ( i x ) FEATURE:
        ( A ) NAME/KEY: P8 primer, sense strand for CNBr
            peptide #2 (SEQ. ID No. 2)
        ( D ) OTHER INFORMATION: RPP is the rubber particle
            protein bound to natural rubber in guayule and
            is essential for rubber formation in guayule ( x i ) SEQUENCE DESCRIPTION: SEQ ID NO: 9:

```
ATG GAR CAR GCN GAR AAR  YT    20
Met Glu Gln Ala Gln Lys Leu
                 5
```

( 2 ) INFORMATION FOR SEQ ID NO: 10:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE:
        ( A ) DESCRIPTION: Oligonucleotide sequence deduced
            from RPP amino acid sequence ( i i i ) HYPOTHETICAL: no ( i v ) ANTI-SENSE: yes ( v i ) ORIGINAL SOURCE:
        ( A ) ORGANISM: Parthenium argentatum
        ( B ) STRAIN: 11591
        ( D ) DEVELOPMENTAL STAGE: cortex from secondary
            growth of stems
        ( F ) TISSUE TYPE: Stembark ( i x ) FEATURE:
        ( A ) NAME/KEY: P3 primer, sense strand for CNBr
            peptide #4 (SEQ. ID No. 4)
        ( D ) OTHER INFORMATION: RPP is the rubber particle
            protein bound to natural rubber in guayule and
            is essential for rubber formation in guayule ( x i ) SEQUENCE DESCRIPTION: SEQ ID NO: 10:

GT Y TCRAA Y T GNRGDAT    17

( 2 ) INFORMATION FOR SEQ ID NO: 11:

(i) SEQUENCE CHARACTERISTICS:
  (A) LENGTH: 92 base pairs
  (B) TYPE: nucleic acid
  (C) STRANDEDNESS: double
  (D) TOPOLOGY: linear (ii) MOLECULE TYPE:
  (A) DESCRIPTION: PCR amplified cDNA from mRNA (iii) HYPOTHETICAL: no (iv) ANTI-SENSE: no (vi) ORIGINAL SOURCE:
  (A) ORGANISM: Parthenium argentatum
  (B) STRAIN: 11591
  (D) DEVELOPMENTAL STAGE: cortex from secondary growth of stems
  (F) TISSUE TYPE: Stembark (ix) FEATURE:
  (A) NAME/KEY: P5/6, a PCR amplified cDNA of CNBr peptide #3 (SEQ ID No: 3) using P5 and P6 primers (SEQ ID Nos: 5 and 6)
  (D) OTHER INFORMATION: RPP is the rubber particle protein bound to natural rubber in guayule and is essential for rubber formation in guayule (xi) SEQUENCE DESCRIPTION: SEQ ID NO: 11:

```
TTC  GGG  TAC  CAA  CCG  TTT  GCA  ACC  AAG  GAC  CCG  AAA  GTA  TTT      42
Phe  Gly  Tyr  Gln  Pro  Phe  Ala  Thr  Lys  Asp  Pro  Lys  Val  Phe
                    5                        10

GAC  CGA  CCT  GAG  GAG  TTT  GTC  CCT  GAT  CGG  TTC  GTT  GGG  GAT      84
Asp  Arg  Pro  Glu  Glu  Phe  Val  Pro  Asp  Arg  Phe  Val  Gly  Asp
15                       20                       25

GGC  GAG  GC                                                              92
Gly  Glu  Ala
     30
```

(2) INFORMATION FOR SEQ ID NO: 12:

(i) SEQUENCE CHARACTERISTICS:
  (A) LENGTH: 1692 base pairs
  (B) TYPE: nucleic acid
  (C) STRANDEDNESS: double
  (D) TOPOLOGY: linear (ii) MOLECULE TYPE:
  (A) DESCRIPTION: cDNA from mRNA (iii) HYPOTHETICAL: no (iv) ANTI-SENSE: no (vi) ORIGINAL SOURCE:
  (A) ORGANISM: Parthenium argentatum
  (B) STRAIN: 11591
  (D) DEVELOPMENTAL STAGE: cortex from secondary growth of stems
  (F) TISSUE TYPE: Stembark (vii) IMMEDIATE SOURCE:
  (A) LIBRARY: Lambda ZAP cDNA library of guayule stembark mRNA
  (B) CLONE: pRPP30

(ix) FEATURE:
  (A) NAME/KEY: pRPP30, a guayule RPP gene
  (C) IDENTIFICATION METHOD: by similarity with known RPP amino acid sequences (SEQ ID Nos: 1, 2, 3 and 4)
  (D) OTHER INFORMATION: Codes for the entire amino acid sequence of RPP which is 473 amino acids long. RPP is the rubber particle protein which is essential for rubber formation in guayule.

( x i ) SEQUENCE DESCRIPTION: SEQ ID NO: 12:

```
CTCACATTCA  AAACAGTCAA  AAC ATG GAC CCA TCG TCT AAA CCC CTC CGT        50
                            Met Asp Pro Ser Ser Lys Pro Leu Arg
                                                   5

GAA ATC CCC GGC TCT TAT GGC ATT CCT TTC TTT CAA CCG ATA AAA            95
Glu Ile Pro Gly Ser Tyr Gly Ile Pro Phe Phe Gln Pro Ile Lys
10              15                  20

GAC CGG TTG GAG TAT TTT TAC GGG ACC GGA GGT CGA GAC GAG TAC           140
Asp Arg Leu Glu Tyr Phe Tyr Gly Thr Gly Gly Arg Asp Glu Tyr
25              30                  35

TTC CGG TCC CGC ATG CAA AAA TAC CAA TCC ACG GTA TTT CGA GCC           185
Phe Arg Ser Arg Met Gln Lys Tyr Gln Ser Thr Val Phe Arg Ala
40              45                  50

AAC ATG CCA CCG GGC CCT TTC GTA AGC AGC AAC CCG AAG GTA ATC           230
Asn Met Pro Pro Gly Pro Phe Val Ser Ser Asn Pro Lys Val Ile
55              60                  65

GTC CTA CTC GAC GCC AAA AGC TTT CCG ATA CTC TTT GAT GTA TCC           275
Val Leu Leu Asp Ala Lys Ser Phe Pro Ile Leu Phe Asp Val Ser
70              75                  80

AAA GTC GAG AAG AAA GAT TTG TTC ACC GGA ACT TAC ATG CCG TCA           320
Lys Val Glu Lys Lys Asp Leu Phe Thr Gly Thr Tyr Met Pro Ser
85              90                  95

ACC AAA CTC ACT GGC GCG TAT CGC GTA CTC TCG TAC CTC GAC CCA           365
Thr Lys Leu Thr Gly Ala Tyr Arg Val Leu Ser Tyr Leu Asp Pro
100             105                 110

TCC GAA CCT AGA CAT GCT CAA CTT AAG AAC CTC TTG TTC TTC ATG           410
Ser Glu Pro Arg His Ala Gln Leu Lys Asn Leu Leu Phe Phe Met
115             120                 125

CTT AAA AAT TCA AGC AAC CGA GTC ATC CCA CAG TTT GAA ACC ACT           455
Leu Lys Asn Ser Ser Asn Arg Val Ile Pro Gln Phe Glu Thr Thr
130             135                 140

TAC ACC GAA CTC TTT GAA GGT CTT GAA GCC GAG CTA GCC AAA AAC           500
Tyr Thr Glu Leu Phe Glu Gly Leu Glu Ala Glu Leu Ala Lys Asn
145             150                 155

GGG AAA GCC GCG TTC AAC GAT GTT GGT GAA CAA GCG GCT TTC CGG           545
Gly Lys Ala Ala Phe Asn Asp Val Gly Glu Gln Ala Ala Phe Arg
160             165                 170

TTT TTG GGC AGG GCT TAT TTT AAC TCG AAC CCG GAA GAA ACC AAA           590
Phe Leu Gly Arg Ala Tyr Phe Asn Ser Asn Pro Glu Glu Thr Lys
175             180                 185

CTA GGA ACT AGT GCG CCT ACG TTA ATT AGC TCG TGG GTG TTA TTT           635
Leu Gly Thr Ser Ala Pro Thr Leu Ile Ser Ser Trp Val Leu Phe
190             195                 200

AAT CTT GCC CCC ACG CTC GAC CTC GGA CTT CCG TGG TTC TTG CAG           680
Asn Leu Ala Pro Thr Leu Asp Leu Gly Leu Pro Trp Phe Leu Gln
205             210                 215

GAA CCT CTT CTA CAC ACT TTC CGA CTG CCG GCG TTC CTG ATT AAG           725
Glu Pro Leu Leu His Thr Phe Arg Leu Pro Ala Phe Leu Ile Lys
220             225                 230

AGT ACT TAC AAC AAA CTT TAC GAT TAT TTC CAG TCG GTT GCG ACT           770
Ser Thr Tyr Asn Lys Leu Tyr Asp Tyr Phe Gln Ser Val Ala Thr
235             240                 245

CCG GTT ATG GAA CAA GCA GAA AAA TTA GGG GTT CCG AAG GAT GAA           815
Pro Val Met Glu Gln Ala Glu Lys Leu Gly Val Pro Lys Asp Glu
250             255                 260

GCT GTG CAC AAT ATC TTA TTC GCG GTT TGC TTC AAT ACT TTT GGT           860
Ala Val His Asn Ile Leu Phe Ala Val Cys Phe Asn Thr Phe Gly
265             270                 275

GGT GTT AAG ATC CTC TTC CCG AAT ACA CTC AAA TGG ATC GGA GTT           905
```

```
Gly Val Lys Ile Leu Phe Pro Asn Thr Leu Lys Trp Ile Gly Val
280             285                 290

GCT GGT GAG AAT TTG CAT ACC CAA TTG GCG GAA GAG ATT AGA GGT       950
Ala Gly Glu Asn Leu His Thr Gln Leu Ala Glu Glu Ile Arg Gly
295             300                 305

GCT ATA AAA TCA TAC GGG GAC GGT AAC GTG ACG CTG GAA GCA ATC       995
Ala Ile Lys Ser Tyr Gly Asp Gly Asn Val Thr Leu Glu Ala Ile
310             315                 320

GAG CAG ATG CCG TTG ACG AAG TCA GTG GTG TAC GAG TCC CTC AGG      1040
Glu Gln Met Pro Leu Thr Lys Ser Val Val Tyr Glu Ser Leu Arg
325             330                 335

ATT GAA CCA CCA GTG CCT CCG CAA TAT GGA AAA GCC AAA AGC AAC      1085
Ile Glu Pro Pro Val Pro Pro Gln Tyr Gly Lys Ala Lys Ser Asn
340             345                 350

TTT ACC ATA GAG TCA CAC GAC GCC ACT TTC GAA GTC AAA AAA GGA      1130
Phe Thr Ile Glu Ser His Asp Ala Thr Phe Glu Val Lys Lys Gly
355             360                 365

GAA ATG TTA TTC GGG TAC CAA CCG TTT GCA ACC AAG GAC CCG AAA      1175
Glu Met Leu Phe Gly Tyr Gln Pro Phe Ala Thr Lys Asp Pro Lys
370             375                 380

GTA TTT GAC CGA CCT GAG GAG TTT GTC CCT GAT CGG TTC GTT GGG      1220
Val Phe Asp Arg Pro Glu Glu Phe Val Pro Asp Arg Phe Val Gly
385             390                 395

GAT GGC GAG GCA TTG TTG AAG TAC GTA TGG TGG TCT AAT GGG CCG      1265
Asp Gly Glu Ala Leu Leu Lys Tyr Val Trp Trp Ser Asn Gly Pro
400             405                 410

GAG ACA GAG AGT CCG ACA GTT GAA AAT AAA CAA TGT GCC GGA AAA      1310
Glu Thr Glu Ser Pro Thr Val Glu Asn Lys Gln Cys Ala Gly Lys
415             420                 425

GAC TTT GTC GTG CTT ATA ACG AGG TTG TTT GTC ATT GAA CTT TTC      1355
Asp Phe Val Val Leu Ile Thr Arg Leu Phe Val Ile Glu Leu Phe
430             435                 440

CGG CGA TAT GAC TCT TTT GAA ATC GAA TTA GGC GAG TCT CCT TTG      1400
Arg Arg Tyr Asp Ser Phe Glu Ile Glu Leu Gly Glu Ser Pro Leu
445             450                 455

GGT GCA GCT GTC ACA CTT ACG TTC CTG AAG AGA GCT AGT ATA TGA      1445
Gly Ala Ala Val Thr Leu Thr Phe Leu Lys Arg Ala Ser Ile
460             465                 470

TTGCAGCCAT AACTAGTTAC CCTGTACTAG CACGTTAGTA AAATGATGTT           1495

TGATATGTTT TTCAAGTAAA TATAAAATA AAGTAATAAA AAAGGGATGT            1545

GTATATGGGG AGGGGTGTGG GAGGTCAGGA TCAAGTATGT ATCAAGGTTG           1595

TTTGTATTAT TCGTGCTATG AATAAGTGTT GAATTTGCAG TTCAAGAGCA           1645

TAAAATAAAT ATTGTTTCAC AAAATTTAGA AAAAAAAAAA AAAAAA               1692
```

RUBBER PARTICLE PROTEIN GENE FROM GUAYULE

This application is a continuation of U.S. patent application Ser. No. 08/000,872, filed Jan. 5, 1993, now abandoned, which was a continuation-in-part of the U.S. patent application Ser. No. 07/687,456, filed Apr. 17, 1991, now abandoned.

The invention described herein was funded in part by grants from the USDA, namely, No. 86-CRCR-1-2211 58-3158-7-11, 88-COOP-12897, and CSRS-90-38200-55668,and from the NSF, namely, MCB-92-20417. The United States Government may have certain rights under the invention.

INTRODUCTION

The present invention relates generally to bioengineering and more particularly to the isolation and elucidation of a guayule rubber particle protein (RPP) gene, the DNA template therefor, and the means, methods and processes to replicate the DNA clone of the guayule RPP gene in both friendly and foreign environments. The invention relates also to the use of this gene and its protein to stimulate rubber biosynthesis in both friendly and foreign environments.

The isolated recombinant vector containing cDNA encoding guayule RPP is transferred to other prokaryotic or eukaryotic host organisms wherein the RPP cDNA is expressed to produce functional RPP for rubber biosynthesis. Rubber biosynthesis occurs as a result of the expression of the recombinant RPP cDNA in the host organism wherein said expression is under the control of a promoter DNA sequence selected from the group consisting of the lacZ promoter, a trp promoter, a trc promoter, a T7 polymerase promoter and other major prokaryotic and eukaryotic operator and promoter regions which increase the expression of foreign genes in procaryotic hosts and the NOS promoter and terminator, the CaMV 35S promoter, the GAL 1 and GAL 10 promoters and other prokaryotic or eukaryotic promoters which increase the expression of genes in eukaryotic cells or their viruses. Rubber biosynthesis occurs as a result of the increased expression of the guayule RPP gene in these host organisms.

BACKGROUND OF THE INVENTION

Rubber is found in more than two thousand plant species, but is limited to only a few plant families (See: Backhaus, *Israel J. Bot.*, 34:283–293 (1985); and Archer et al., *Chemistry and Physics of Rubber-like Substances*, Bateman, L. ed., pp 41–72, MacLaren, London (1963)). Rubber is a polymer composed of between 320–35,000 isoprene molecules. These are linked by stepwise, head-to-tail, cis-1,4 condensations that form the polyisoprene chains. The stepwise isoprene additions are performed by a prenyltransferase enzyme [E.C. 2.5.1.20] known as rubber transferase (RUT), rubber polymerase and rubber cis, 1–4 polyprenyl transferase. RuT has been ascribed as the sole enzyme responsible for rubber formation in plants (See: Backhaus, *Israel J. Bot.* 34: 283–293, (1985); Berndt, *U.S. Government Res. Rep.* AD-601, 729, (1963), Archer and Cockbain, *Methods in Enzymology*, 15:476–480, (1969) Archer and Audley, *Advances in Enzymology*, 29:221–257, (1967) and Lynen, *Rubber Res. Inst. Malaya*, 21:(4) 389–406, (1969)). However, as this patent application will show, there is another enzyme, known as RPP (for rubber particle protein) that clearly causes rubber biosynthesis when transferred to a foreign host plant, which in our case, is tobacco. As this patent application will show, RPP, unlike RuT, is not a prenyltransferase, but an unusual form of allene oxide synthase (AOS) which is a member of a class of cytochrome P450, heme-binding enzymes. We will show that RPP has properties similar to other members of this class of heme-binding enzymes and that it is an enzyme responsible for rubber biosynthesis. P450 enzymes have never before been implicated in rubber biosynthesis. We will describe the construction of a binary vector, named pBIRPP, which contains the RPP gene and will show that when the RPP gene is transferred to tobacco and expressed, it produces functional RPP enzyme. The resulting RPP enzyme produced in these transgenic plants causes rubber biosynthesis and the rubber so produced accumulates in rubber particles in the cells of these plants. We predict that guayule RPP and its homologues from other rubber-producing species are the enzymes responsible for rubber biosynthesis in plants.

The enzymatic activity of RPP has never been elucidated until now. Spectral analysis will be described which confirms that RPP is a cytochrome P450. It will be shown that RPP is a non-mono-oxygenase type of heme-binding protein and is not a prenyltransferase. Knowledge of such a role for P450 in rubber has never before been described. Biochemical analyses will show that RPP metabolizes lipid hydroperoxides into lipid epoxides and does not perform prenyltransferase-type reactions. This patent application goes on to describe the means and methods for isolating a full-length cDNA for the guayule RPP gene. It describes the DNA and amino acid sequence for RPP and demonstrates a method for inserting the RPP cDNA downstream of a strong eukaryotic CaMV 35S plant promoter in the pBIRRP binary vector. It describes how this vector is used to create transgenic tobacco plants which then produce functional RPP. These transgenic tobacco plants express the foreign RPP gene contained in the pBIRPP vector and carry out rubber biosynthesis. Rubber is observed as rubber particles which accumulate in tobacco cells. These particles resemble those observed in guayule cells. The invention verifies that RPP, encoded by a single nuclear gene, is responsible for rubber biosynthesis in plants. Moreover, it suggests that the mechanism of rubber formation is not based solely on the presence a RuT-type, cis-prenyl-transferase enzyme, as originally thought, but also requires a RPP-type, cytochrome P450, heme-binding enzyme.

The first identification of guayule RPP was made in 1985 (Backhaus and Chandra, in Alcorn, S. and Fangmeier, D. (eds) *Proceedings of the 4th International Guayule Conference on Guayule Research and Development*, Oct. 16–19, (1985); Backhaus and Bess, in Randall, D. D. et al. (eds) *Current Topics in Plant Biochemistry and Physiology*, Vol 5:186 (1986)). Subsequent publications described its purification and characterization and suggested a putative role as a prenyltransferase in guayule rubber particles (Backhaus and Bess, in Benedict, C. R. (ed) *Biochemistry and Regulation of cis-Polyisoprene in Plants*, NSF sponsored workshop publication, p. 204–220 (1986); Cornish and Backhaus, *Phytochem.* 29:3809–3813, (1990); and Backhaus et al. *Phytochem.* 30:2493–2497 (1991)). Work by Cornish and Siler demonstrated that RPP-like proteins were also present in Hevea and Ficus (Siler and Cornish, *Phytochem.* 32: 1097–1102 (1993); Cornish, et al. *J. Nat. Rubb. Res.* (1994) (in press); Cornish, et al., *Phytochem.* (in press) (1994); Siler and Cornish, *Phytochem.* (1994)(in press)). The RPP-like proteins in rubber particles of these other species are likely involved in the same enzymatic reaction as RPP. These are the only known citations in the literature that specifically refer to RPP. Reference to another protein isolated from guayule rubber particles was made (Benedict et al. *Plant Physiol.* 92:816–821 (1990)) which described a prenyl-transferase but did not identify that protein as RPP despite prior knowledge by those authors (cf. Benedict, C. R. (ed) *Biochemistry and Regulation of cis-Poly-isoprene in Plants*, NSF sponsored workshop publication, p. 204–220 (1986)) of RPP's existence in guayule rubber particles. The first identification and verification of RPP as a cytochrome P450 necessary for rubber biosynthesis is this patent application.

The molecular cloning of RPP is described herein. Prior to this, its molecular weight was estimated to be 48,500 to 53,000 Daltons as determined by sodium dodecylsulfate polyacrylamide gel electrophoresis (SDS-PAGE). Other characteristics of RPP includes its amino acid composition, its isoelectric point (pI=6.2), that it is a glycoprotein and how it is assembled in rubber particles as a membrane protein (Backhaus et al., *Phytochem.* 30:2493–2497 (1991)). In this patent application we further describe its amino acid sequence, its biochemical function and the consequences of its expression in tobacco, a non-rubber producing species.

RPP is the most abundant protein of guayule rubber particles (Backhaus et al., *Phytochem.* 30: 2493–2497 (1991)) and was, therefore, considered to be important for rubber biosynthesis. For this reason, the cDNA for the RPP gene was targeted for isolation from guayule stembark, with the intent of using the gene to induce rubber biosynthesis in a variety of other organisms that do not ordinarily synthesize rubber. This invention teaches that this occurs when the RPP gene is placed in a binary plasmid vector under the control of a strong promoter and is transferred to a new host (tobacco) which expresses the RPP gene and produces functional RPP enzyme. Conversely, the gene can also be placed in other plants, such as guayule or Hevea, that already synthesize rubber with the intent of overexpressing RPP. The overexpressed RPP can then enhance rubber production in these plants. Additionally, RPP could be transferred to and expressed in other eukaryotic organisms or cell cultures including yeast, insects or higher animals or in prokaryotic organisms, with the intent of producing rubber. This patent application seeks to protect the invention of the isolated DNA molecule for the RPP gene from guayule and demonstrates that this gene can generate rubber biosynthesis in those transgenic organisms (ie., tobacco) when that foreign RPP gene is expressed.

BRIEF SUMMARY OF THE INVENTION

The RPP gene and the DNA template thereof are isolated and elucidated. The full-length cDNA clone of the abundant guayule RPP gene has been isolated and is described. It has been named pRPP30.

This invention will teach that RPP from guayule rubber particles is not a prenyl-transferase. Instead it is a non-monooxygenase, cytochrome P450, heme-binding protein that generates lipid epoxides from lipid hydroperoxides. This invention will teach how this enzyme is purified from guayule rubber particles and how its activity is measured. It will teach how the amino acid sequence for the pure protein is determined and how this sequence information is used to isolate the cDNA for RPP from a guayule stembark cDNA library. It will teach how the guayule stembark cDNA library is prepared and it will teach the DNA and amino acid sequence for the full-length cDNA clone of RPP. It will teach the similarities and differences between RPP and another non-monooxygenase, heme-binding protein known as allene oxide synthase (AOS). AOS is an enzyme that is found in several monocotyledonous plants. These species do not produce rubber, and so their form of AOS is not involved in rubber synthesis in those species. This is possibly due to the structural differences between RPP and AOS.

This invention will further teach how the RPP cDNA is constructed in the new binary vector (pBIRPP) by inserting RPP downstream of the strong, constitutive 35S plant promoter. It will teach how this binary vector is used to transfer the RPP cDNA into tobacco using Agrobacterium. This invention will also teach that the foreign RPP gene is transcribed, translated and expressed as a fully functional RPP with AOS-like enzymatic activity. This invention also teaches that this activity is present only in tobacco transformed with RPP and is absent in non-transformed tobacco. It will teach that the expression of this functional enzyme causes rubber biosynthesis in those transgenic tobacco plants and that this rubber is deposited and accumulated in rubber particles within the cells of those plants. Finally, it will teach that these rubber particles can be observed by both electron and light microscopy. In view of its ability to generate rubber biosynthesis in tobacco, it is readily apparent that the transfer and expression of the RPP gene to other hosts should also lead to rubber biosynthesis in those other organisms as well.

The exact mechanism for RPP's role in rubber biosynthesis is not yet understood. Unlike RuT, RPP is not involved with the sequential, cis-polymerizations of isoprene from IPP (see FIG. 6B). Rather, RPP is involved in epoxide formation, possibly of the isoprene groups in the polyisoprene chain. Epoxides are ubiquitous in isoprene chains of natural rubber (Burfield, *Nature* 249:29–30 (1974); Burfield, *J. Nat. Rubb. Res.* 1:202–208 (1986); Burfield, et al. *Polymer* 17:713–716 (1976); Burfield and Eng, *Polymer* 30:2019–2022 (1989); Burfield and Gan, *Polymer* 18:607–611 (1977); Burfield and Gan, *J. Polymer Sci., Polymer Chem. Edn.* 13:2725–2734 (1975); Burfield and Gan, *J. Polymer Sci., Polymer Chem. Edn.* 15:2721–2730 (1977)) and serve as sites of crosslinking in rubber molecules. Burfield proposed that a latex enzyme was responsible for such epoxidation in rubber molecules. It has always been assumed that the very high molecular weight rubbers, in excess of 100,000 to 1,000,000 Daltons, are composed of linear chains containing one long molecule of polyisoprene. This led to the theory that rubber formation was due solely to a single prenyltransferase enzyme that carried out this step-wise, linear chain elongation. However, one alternative hypothesis suggested that rubber was actually formed as a consequence of crosslinking between small polyisoprene chains to generate high molecular weight isoprenoids (Westall, *Polymer* 9:243–248). This could explain why a bimodal molecular weight distribution is always observed in natural rubber, because separate pools of small and large polyisoprenes exist in the same plant. In principle, the small chains combine by crosslinking to make larger Polymers. This is partially supported by genetic evidence which shows that unique and reproducible bimodal molecular weight distributions are obtained for rubber from clonally propagated Hevea (Subramaniam, *Proceedings of the International Rubber Conference* Kuala Lumpur, vol.4, p.3–27, (1975)) and guayule (Backhaus and Nakayama *Rubber Chem. Technol.,* 61:78–85 (1988)). We now believe that rubber is assembled by a mechanism, such that small chain isoprenes are crosslinked to form large molecular weight rubber polymers and that RPP plays a fundamental role in this process. This would suggest that small, linear cis-polyisoprenes, containing between 20–320 isoprenes, are present and available in plants for this crosslinking to occur. This has, in fact, been demonstrated for a wide number of non-rubber producing plants, such as gymnosperms, birch, and members of the rose family, which accumulate cis-polyprenols containing up to 50 or more isoprenes but do not synthesize rubber (Swiezewska, et al. *Biochem. Cell Biol.* 70:448–454 (1992)). It may be that these species can not produce rubber because they lack the enzyme to crosslink the small polyisoprenes into larger ones. We believe that this may be the function of RPP; by forming epoxides in small polyisoprenes which serve as sites to crosslink rubber. Regardless of this hypothetical function, our invention clearly demonstrates that if the RPP enzyme is introduced into a non-rubber producing tobacco plant, that plant goes on to synthesize rubber.

The first step in developing this patent was to isolate a cDNA clone for the RPP gene. The strategy was to use amino acid sequence data from pure RPP to generate DNA probes to screen a cDNA library. To do this, RPP was purified to homogeneity and cleaved with CNBr. RPP was cleaved into 4 distinct fragments which were sequenced from their N-termini (FIG. 1). Oligonucleotides corresponding to the known protein sequences were synthesized (FIG. 2) and used to prime plus and minus strand amplification of guayule bark cDNA, via the Polymerase chain reaction (PCR). Using primers 5 and 6 we obtained a 92 bp fragment of DNA which, upon sequencing, matched perfectly with the known protein sequence of peptide fragment #3 of RPP (FIG. 2). This 92 bp probe was then used to screen a lambda ZAP, stembark cDNA library. Positive clones were rescreened at least two times with radioactive probes to verify hybridization. Forty five cDNA clones were obtained which contained RPP cDNAs of various lengths. The four longest clones were sequenced and found to be identical in their protein coding region and all contained DNA sequences coding for the four CNBr fragments shown in FIG. 1. The order of those fragments in the protein sequence was #4, #2, #1, and #3 respectively (FIGS. 3 and 4), going from the 5' to 3' direction of the gene. The RPP cDNA clone described in this application is one of the four full-length clones isolated. It is named pRPP30 and is shown in FIGS. 3 and 4. The pRPP30 gene is 1692 bp long and contains an open reading frame of 1419 bp for RPP. The 1419 bp open reading frame encodes a 473 amino acid sequence equivalent to 53,438 Daltons and includes 8 methionines and 2 cysteines. The deduced pI of the 473 amino acid protein is 6.15, which agrees with the experimental value of 6.2 for RPP (Backhaus et al. *Phytochem.* 30:2493–2497 (1991)). There are 3 potential N-linked, glycosylation sites in RPP of sequence Asn-X-Ser/Thr, wherein X can be any of the common 20 amino acids. In addition, pRPP30 contains a stop codon (TGA), a 5'-noncoding region of 23 bp and a 3'-noncoding region of 250 bp. The pRPP30 cDNA is composed of the 1692 bp RPP gene contained within a Bluescript SK- (Stratagene, Inc) phagemid. This phagemid is a well-known and commercially available cloning vector. The pRPP30 cDNA phagemid is a 4631 bp circular molecule, of which 1692 bp is the RPP gene inserted between the unique EcoR1 and Xho1 cloning sites of that vector. A map of the pRPP30 is shown (FIG. 4)

The original source of material for isolating the pRPP30 cDNA molecule was stembark tissue from the 11591 line of guayule shrubs. This tissue is rich in natural rubber and is readily available from guayule field plots growing in and around the Phoenix metropolitan area. The lambda ZAP cDNA cloning system used herein is a well-known and commonly available lambda phage expression vector. Its construction and restriction endonuclease map are described by Short, et al. *Nucl. Acids Res.* 16:7583–7600, (1988); Huse and Hansen, *Strategies* 1:1–3; Sorge, *Strategies* 1:3–7 (1988); and associated techniques in Gubler and Hoffman, *Gene* 25:263 (1983); Young and Davis, *Proc. Natl. Acad. Sci. U.S.A.* 80:1194–1198 (1983); and Watson and Jackson, *DNA cloning; A practical approach* 79–88, (1985).

A computer based search using the WORD, FASTA and TFASTA algorithms was not able to identify significant homology to the pRPP30 sequence with any of the known sequences in the GENBANK/EMBL and SWISSPROT databanks. Direct comparison to published sequences for the Hevea rubber elongation factor (Dennis and Light, *J. Biol. Chem.* 264: 18618–18626 (1989); Attanyaka et al., *Plant Mol. Biol.* 16: 1079–1081 (1991); Goyvaerts et al., *Plant Physiol.* 97:317–321 (1991)) also showed no homology. Although it was anticipated that RPP would share homology or structural domains to one or more of the known prenyltransferases (Kuntz et al. *Plant J.* 2:25–34 (1992)), this proved negative. Sequence comparison using the BLAST algorithm (Altschul et al. *J. Mol. Biol.* 215: 403–410, (1990)) finally revealed significant homology to portions of several cytochrome P450s. Small regions of homology to RPP were detected in the two conserved "B" and "C" domains of P450s (Kalb and Loper, *Proc. Natl. Sci. USA* 85: 7221–7225 (1988)) but RPP lacked homology to the "A" and "D" domains. The highly conserved "D" domain is especially critical for most P450s. This apparent structural anomaly was resolved when the sequence for another unusual P450, allene oxide synthase (AOS), from flaxseed, was published (Song et al., *Proc. Natl. Acad. Sci. U.S.A.*, 90: 8519–8523 (1993)).

Comparison of RPP and AOS (FIG. 5) shows over 65% homology and 85% similarity between the two protein sequences. Both have several structural features in common, especially their unusual heme-binding site within the "D" domain. However, unlike AOS, RPP does not possess a transit signal peptide. AOS is thought to be localized in plastids while RPP is not. This difference in N-termini may explain why RPP is localized in rubber particles and not in plastids. Allene oxide synthase is a non-monooxygenase type of P450 that is responsible for epoxide formation in lipids (Song and Brash, *Science*, 253: 781–783 (1991); Lau, et al., *Biochem.*, 32: 1945–1950 (1993); Vick, in *Lipid Metabolism in Plants*, T. S. Moore, Ed. (CRC Press, Boca Raton, p. 167–191 (1993); (Zimmerman, *Biochem. Biophys. Res. Comm.* 23:398–403 (1966); Zimmerman and Feng, *Lipids* 13:313–316 (1978); Zimmerman and Vick, *Plant. Physiol.* 46:445–453 (1970)). Its function in those plants is believed to be involved with the production of prostaglandin-like compounds in plants, such as jasmonic acid.

Since there was a possibility that RPP was a member of this group of enzymes, biochemical analyses were performed on RPP purified from rubber particles. Three-times, washed rubber particles were prepared by centrifugation according to Cornish and Backhaus, op cit.(1990) from a crude homogenate of guayule stembark. RPP was solubilized by sonicating washed particles in 0.5% CHAPS and passing that solution through a 0.22 μm filter to remove all remaining rubber particles. Protein gels revealed the extent of purification for each of the steps from crude homogenate (FIG. 6A, lane 1), to washed rubber particles (FIG. 6A, lane 2) to the final filtered, CHAPS extract (FIG. 6A, lane 3). Prenyltransferase activity was determined for each purification step by measuring the incorporation of $^{14}$C-isopentenyl pyrophosphate into isoprenoid derivatives that were analyzed by TLC (benzene/ethyl acetate, 90/10) and autoradiography (Dogbo and Camara, *Plant Sci.* 49: 103–109

(1987); Kuntz et al. *Plant J.* 2:25–34 (1992)). Dimethylallyl pyrophosphate (DMAPP) was used as the initiator to measure activity in 100 µl aliquots of proteins from each of the three steps (FIG. 6B, lanes 1–3). TLC analysis revealed the complete absence of prenyltransferase activity in the filtered RPP preparations, in which all of the rubber particles had been removed. However, prenyltransferase activity was present in both the crude homogenate and washed preparations containing rubber particles (cf. FIG. 6B, lane 3 with lanes 1 and 2). These prenyltransferases synthesized several isoprenoid derivatives including geranyl pyrophosphate, farnesyl pyrophosphate, geranylgeranyl pyrophosphate, phytoene, squalene and other unidentified, higher order isoprenes. However no isoprenoids of any kind were produced by the CHAPS-solubilized, filtered preparations of RPP (FIG. 6B, lane 3).

Spectral analysis of this CHAPS-solubilized, filtered RPP preparations revealed that RPP was a cytochrome P450. A difference spectra of this extract clearly indicated a characteristic peak at 450 nm (arrow, FIG. 6C). To confirm that RPP was an allene oxide synthase, an aliquot of this preparation was used in an assay that measured the degradation of linoleic hydroperoxide (LOOH) which has an absorbance maximum at 234 nm. This substrate was prepared according to Zimmerman (Zimmerman, *Biochem. Biophys. Res. Comm.* 23:398–403 (1966); Zimmerman and Feng, *Lipids* 13:313–316 (1978); Zimmerman and Vick, *Plant. Physiol.* 46:445–453 (1970)). The reaction was initiated by the addition of pure RPP to a cuvette containing LOOH and then scanning the cuvette with a series of UV spectra at 10 sec intervals (Song and Brash, *Science* 253: 781–784 (1991). Results showed that purified RPP had high AOS activity (FIG. 6D). This biochemical activity was similar to the activity of flaxseed AOS and was consistent with sequence data suggesting similar functions for the two proteins. Furthermore, the data clearly showed that RPP was not a prenyltransferase.

In order to test the effect of RPP expression in transgenic tobacco, a 12.8 kb binary vector was constructed with the RPP gene downstream of the 35S promoter and upstream of the NOS terminator. That vector, named pBIRPP (FIG. 7), was mobilized into *Agrobacterium tumefaciens* strain LBA 4404 which was used to transform tobacco cv. Samsun plants. A second construct containing RPP in the antisense orientation was also prepared. Transformed tobacco plants were selected on kanamycin and grown to maturity. Analyses revealed the presence and expression of the foreign RPP gene (FIG. 8) in transformed tobacco plants. SDS gels (FIG. 8A) of total tobacco proteins showed the presence of RPP (arrow) in 4 different transformants (#3, #6, #14, and #17) and its absence in non-transformed, control (C) and antisense (A) tobacco. A Western hybridization of an identical gel (FIG. 8B) probed with a mono-specific RPP-antibody showed a single RPP band (arrow) in each of the sense constructs (#3, #6, #14, #17) and its absence in control (C) and antisense (A) tobacco constructs. Further enzymatic analysis of protein extracts prepared from control (C) and transformed (#3) tobacco showed that strong AOS activity, due to the expression and production of functional RPP from the foreign gene, was present only in transformed tobacco (FIG. 8D) and was completely absent in control tobacco (FIG. 8C). Because control plants do not contain the RPP gene and do not produce any functional RPP enzyme they are unable to metabolize LOOH. The UV scans of extracts prepared from transgenic tobacco, however, reveal that they possess high AOS activity because they express the recombinant RPP gene.

Since it was established that the transformed tobacco plants produced RPP, their tissues were examined microscopically for any evidence of rubber production. Electron microscopy is the most sensitive means of detecting rubber particles. Electron micrographs of tobacco stems revealed that rubber particles were not produced in non-transformed, control plants (FIG. 9A) but were produced in transformed plants (FIGS. 9B and 9C). The tobacco rubber particles (arrows) bear a striking resemblance to guayule rubber particles (Backhaus and Walsh, *Bot Gaz.* 144: 391–400, 1983)) and occur primarily in plant vacuoles. This is the first report of rubber biosynthesis in a non-rubber producing plant due to transgene manipulation.

Further verification for rubber production in transgenic tobacco was obtained by light microscopy using a highly specific stain for rubber (Addicott, *Stain Technol.* 19:99–102 (1944)). This stain is only effective when relatively high concentrations of rubber are produced in the tissues. Again, as with the electron micrographs, light micrographs show no rubber in cells of non-transformed plants (FIG. 10A), but show abundant rubber in cells of transformed plants (FIG. 10B). The rubber appears as dark blue staining globules within the cells (arrows). These rubber producing cells are not distributed uniformly throughout the plant, but are concentrated in the outer layers of the stem. It is believed that these cells produce certain precursors, perhaps small chain polyisoprenes, that are needed for high molecular weight rubber synthesis. Regardless, it is clear that RPP is crucial for eliciting rubber biosynthesis in this species.

The cloning of the cDNA for RPP and the elucidation of its protein sequence and structural domains, as disclosed herein, will permit structure-functional analysis and provide a foundation for determining its role in rubber biosynthesis in guayule and other organisms. As demonstrated herein, RPP is shown not to be a prenyltransferase but a non-monooxygenase type of cytochrome P450. RPP can form lipid epoxides from lipid hydroperoxides, and this appears to be crucial for high molecular weight rubber biosynthesis. Also, the expression of RPP in a natural or foreign host can be regulated by placing the pRPP30 cDNA downstream of an appropriate 5' promoter and transferring that recombinant gene to the genome of another host. The expression of functional RPP enzyme can be followed by a sensitive biochemical assay which monitors the rapid degradation of LOOH in the presence of RPP. The effect of RPP gene expression on rubber biosynthesis is also demonstrated by electron and light microscopy of transgenic plants. This invention is thus important to the agricultural, biological and chemical sciences and offers a basis for natural rubber production in a wide range of organisms, including prokaryotic or eukaryotic species using recombinant DNA methods. A DNA sequence encoding RPP or its protein are disclosed.

Accordingly, a primary object of the present invention is to provide DNA sequences and recombinant DNA molecules coding for RPP.

Another object of the present invention is to provide new and improved processes for the production of RPP polypeptides from DNA sequences and recombinant DNA molecules coding for RPP.

A further object of the present invention is to provide vectors containing the proper DNA molecules coding for RPP and the cultures to produce recombinant rubber particle protein.

A further object is to use the recombinant RPP for stimulating rubber synthesis in other host organisms.

These and still further objects as shall hereinafter appear are readily fulfilled by the present invention in a remarkably unexpected manner as will be readily discerned from the following detailed description of an exemplary embodiment thereof, especially when read in conjunction with the accompanying drawings.

BRIEF DESCRIPTION OF THE DRAWINGS

The file of this patent contains at least one drawing(s) executed in color. Copies of this patent with color drawing (s) will be provided by the Patent and Trademark Office upon request and payment of the necessary fee.

In the drawings:

FIG. 1 depicts the amino acid sequences of four different fragments obtained from a cyanogen bromide digest of purified guayule rubber particle protein;

FIG. 2A–B (collectively referred to herein as FIG. 2) displays the chemically synthesized oligonucleotide DNA probes and/or primers used in accordance with the present invention;

FIG. 3A–G (collectively referred to as FIG. 3) displays the full-length nucleotide sequence of the pRPP30 cDNA clone of guayule rubber particle protein gene of the present invention (* denotes known amino acid sequences of CNBr fragments of RPP; → denotes the position of chemically synthesized oligonucleotide, sense-strand probes used to amplify RPP cDNA by polymerase chain reaction; ← denotes the position of chemically synthesized oligonucleotide, antisense-strand probes used to amplify RPP cDNA by polymerase chain reaction);

FIG. 5 displays the amino acid sequence comparison of RPP with flaxseed AOS showing 65% identity and 80% similarity;

FIG. 6A is a coomassie blue, stained, SDS gel showing each of the purification steps leading to purified RPP. Lane 1 contains crude homogenate; lane 2 contains 3× washed rubber particles; lane 3 contains the 0.5%, CHAPS solubilized RPP, filtered a through Millipore, Millex-GV, 0.22 um, SLGV filter which removes all of the remaining rubber particles; lane M contains the molecular weight markers. FIG. 6B is an autoradiograph of a TCL plate showing products of prenyltransferase activity from each purification step from lanes 1, 2 and 3, panel A. Aliquots from each purification step were incubated with $^{14}$C-IPP, DMAPP, $Mg^{+2}$ and $Mn^{+2}$ to yield isoprenes of various chain-lengths as shown (arrows): SQ, squalene; P, phytoene; X, unknown isoprenes; GG, geranylgeraniol; F, farnesol; G, geraniol; O, origin. Note that pure RPP in lane 3 synthesizes no isoprenes compared to the crude homogenate in lane 1 and washed rubber particles in lane 2. FIG. 6C is a difference spectra of the pure CHAPS-solubilized, filtered RPP from lane 3, Panel A. Reference and sample cuvettes were reduced with sodium dithionite and the sample cuvette was bubbled with CO to produce a characteristic peak at 450 nm (arrow). FIG. 6D shows AOS-like activity in an aliquot of pure, CHAPS-solubilized, filterd RPP from lane 3, Panel A. Activity is measured by repetitive UV scans at 10 sec intervals showing the disappearance of linoleic acid hydroperoxide (LOOH) which has an absorbance maximum at 234 nm. Upon addition of pure RPP to the cuvette, LOOH is rapidly metabolized to allene oxide, observed by a decrease in absorbance at 234 nm. Complete disappearance of LOOH occurs after 10 minutes;

FIG. 8 displays the biochemical analyses of tobacco plants transformed with the pBIRPP binary vector that produces functional RPP.

DESCRIPTION OF PREFERRED EMBODIMENTS

Figure 4:
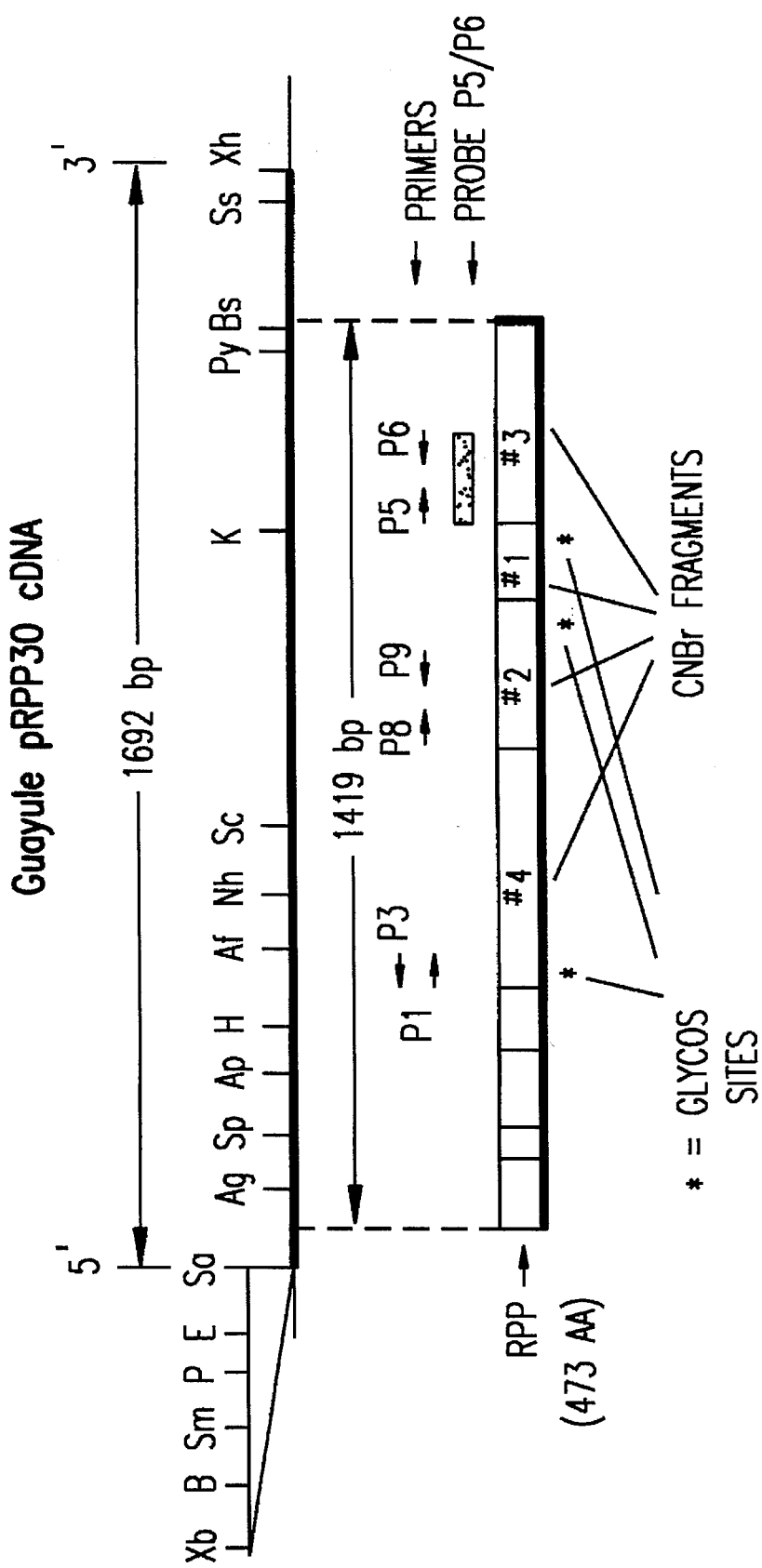
FIG. 4 displays a map of the guayule RPP cDNA in pRPP30 depicting restriction endonuclease sites; the position of primers P1, P3, P8, P9, P5, P6 and the PCR generated P5/P6, 92 bp probe; the positions of the CNBr peptide fragments #1, #2, #3 and #4; and the potential N-linked glycosylation sites (*) (Abbreviations: Af=AflII; Ag=AgeI; Ap=ApaI; B=BamHI; Bs=BsgI; H=HindIII; K=KpnI; Nh=NheI; P=PstI; Pv=PvuII; Sa=SacI; Sc=ScaI; Sm=SmaI; Sp=SphI; Ss=SspI; Xb=XbaI; Xh=XhoI)
Figure 6A:
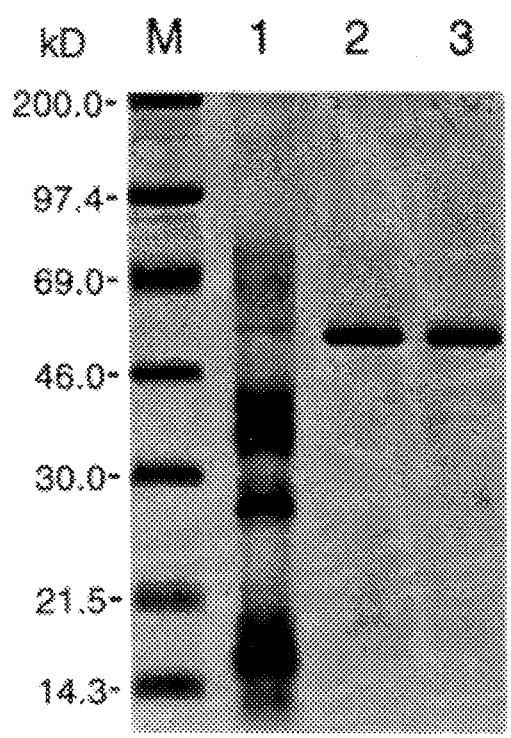
FIG. 6A–D displays the biochemical analysis of RPP purified from guayule rubber particles.
Figure 6B:
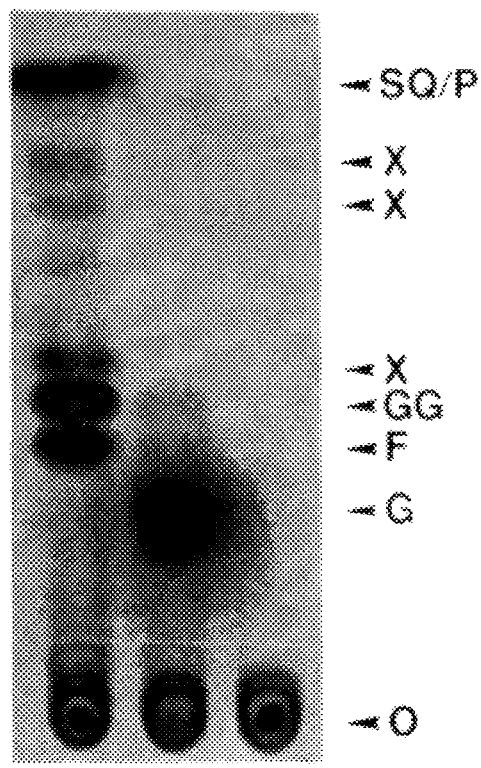
Figure 6D:
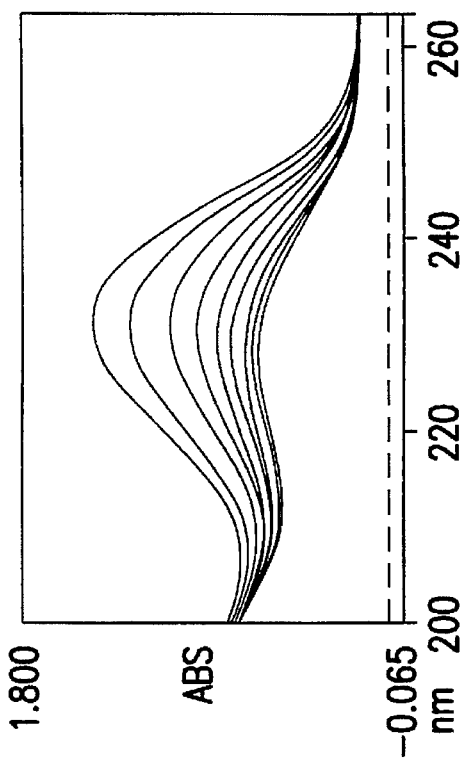
Figure 6C:
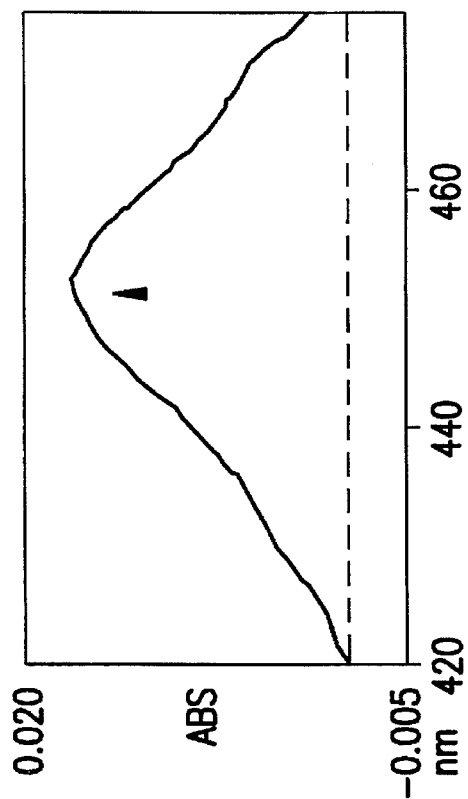

In order that the invention herein described may be fully understood, the following definitions are provided.

Nucleotide means a monomeric unit of DNA or RNA consisting of a sugar moiety (Pentose), a phosphate, and a nitrogenous heterocyclic base. The base is linked to the sugar moiety via the glycosidic carbon (1' carbon of the pentose) and that combination of base and sugar is called a "nucleoside". The base characterizes the nucleotide. The four DNA bases are adenine ("A"), guanine ("G"), cytosine ("C"), and thymine ("T"). The four RNA bases are A, G, C, and uracil ("U"). As is conventional for convenience in the structural representation of a DNA nucleotide sequence only one strand is shown in which A on one strand connotes T on its complement and G connotes C. Amino acids are shown either by a three letter or one letter abbreviation as follows:

| Abbreviated Designations | Amino Acid |
| --- | --- |
| A Ala | Alanine |
| C Cys | Cysteine |
| D Asp | Aspartic acid |
| E Glu | Glutamic acid |
| F Phe | Phenylalanine |
| G Gly | Glycine |
| H His | Histidine |
| I Ile | Isoleucine |
| K Lys | Lysine |
| L Leu | Leucine |
| M Met | Methionine |
| N Asn | Asparagine |
| P Pro | Proline |
| Q Gln | Glutamine |
| R Arg | Arginine |
| S Ser | Serine |
| T Thr | Threonine |
| V Val | Valine |
| W Trp | Tryptophan |
| Y Tyr | Tyrosine |

DNA Sequence means a linear array of nucleotides connected one to the other by phosphodiester bonds between the 3' and 5' carbons of adjacent pentoses.

Codon means a DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame means the grouping of codons during the translation of mRNA into amino acid sequences. During translation the proper reading frame must be maintained. For example, the DNA sequence GCTGGTTGTAAG may be expressed in three reading frames or phases, each of which affords a different amino acid sequence:

GCT GGT TCT AAG -Ala-Gly-Cys-Lys

G CTG GTT GTA AG -Leu-Val-Val

GC TGG TTG TAA G -Trp-Leu-(STOP)

Polypeptide and peptide means a linear array of amino acids connected one to the other by peptide bonds between the alpha-amino and carboxyl groups of adjacent amino acids.

Genome means the entire DNA of a cell or a virus. It includes, inter alia, the structural gene coding for the polypeptides of the substance, as well as operator, promoter, terminator, enhancer and ribosome binding and interaction sequences.

Gene means a DNA sequence which encodes through its template or messenger RNA ("mRNA") a sequence of amino acids characteristic of a specific polypeptide.

cDNA means a complementary or copy DNA prepared by using mRNA as a template for synthesizing the first strand of DNA using reverse transcriptase, an appropriate oligonucleotide primer and a mixture of nucleotides.

PCR means a Polymerase chain reaction whereby a specific DNA sequence, either genomic or cDNA, can be preferentially amplified by the enzyme Taq Polymerase using synthetic, oligonucleotide sense and antisense primers, (which specify a target sequence), a mixture of nucleotides and a temperature thermocycling regime which allows sequential denaturing, annealing and synthesis of the target DNA between the primers.

Transcription means the process of producing mRNA from a gene or DNA sequence.

Translation means the process of producing a polypeptide from mRNA.

Expression means the process undergone by a gene or DNA sequence to produce a polypeptide and comprises a combination of transcription and translation.

Plasmid or phagemid means a nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for ampicillin resistance ($AMP^R$) transforms a cell previously sensitive to ampicillin into one which is resistant to it. A cell transformed by a plasmid is called a "transformant".

Phage or Baoteriophage means a bacterial virus, many of which consist of DNA sequences encapsidated in a protein envelope or coat ("capsid").

Cloning Vehicle means a plasmid, phagemid, binary vector, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., ampicillin resistance. A cloning vehicle is often called a vector.

Cloning means the process of obtaining a population of organisms or DNA sequences derived from one such organism or sequence by asexual reproduction.

Recombinant DNA Molecule or Hybrid DNA means a molecule consisting of segments of DNA from different genomes which have been joined end-to-end outside of living cells and able to be maintained in living cells.

Expression Control Sequence means a sequence of nucleotides that controls and regulates expression of genes when operatively linked to those genes. They include but are not limited to the lacZ promoter, the trp promoter, the tac and trc promoter, the T7 Polymerase promoter and other major prokaryotic and eukaryotic promoters which increase expression of foreign genes in prokaryotic hosts and the NOS promoter and terminator, the CaMV 35S promoter and other prokaryotic and eukaryotic promoters which increase the expression of genes in eukaryotic cells or their viruses or combinations thereof.

Guayule rubber particle protein (RPP), is a polypeptide of 53,500 Daltons, localized in the rubber particles of guayule. It is a non-mono-oxygenase, cytochrome P450 heme-binding protein which has an essential function for rubber biosythesis in plants which is believed to be involved with epoxide formation.

The present invention relates to DNA sequences and recombinant DNA molecules coding for the guayule RPP and processes for the production of those polypeptides, to recombinant expression systems for these sequences, to vectors containing them, to cultures producing the recombinant protein, and to the materials significant in its production. A DNA sequence encoding guayule RPP or a protein having substantially the same biological activity for rubber biosynthesis as guayule RPP is shown.

The isolated recombinant vector containing cDNA encoding the guayule rubber particle protein (RPP) is transferable to other prokaryotic or eukaryotic host organisms wherein the RPP DNA will be expressed to produce functional RPP for rubber biosynthesis. Rubber biosynthesis occurs as a result of the recombinant RPP vector DNA expression in these host organisms.

Although a variety of selection and DNA cloning techniques might potentially have been employed in our isolating and cloning of a DNA sequence of this invention, a selection strategy based on purified RPP was adopted.

Purification and CNBr cleavage of RPP.

The source of RPP is from purified rubber particles which are isolated from guayule line 11591 stembark tissues by the procedure described by Cornish and Backhaus, op cit, (1990) and Backhaus et al., op cit, (1991). Purified rubber particles are subjected to preparative SDS-PAGE to purify RPP, which is observed in the gel as a protein band migrating with an apparent molecular weight of 48,500–53,500 Daltons. RPP is purified from gel bands by electroelution using a Model 422 Electroeluter (Bio-Rad) according to manufacturer's instructions.

Purified RPP equivalent to at least 1000 pmoles was taken to dryness by lyophilization and dissolved in 150 µl 70% formic acid in an Eppendorf tube. To this 100 µl of 70 µg/mL CNBr in 70% formic acid was added. The mixture was incubated in the dark at room temperature for 24 hours. The CNBr digested RPP was subjected to SDS-PAGE using a 16% acrylamide gel in a Tris-Tricine, 3-layer system as described by Schagger and Von Jagow, *Anal. Biochem* 166:368–379, (1987). Following electrophoresis, protein fragments were blotted onto PVDF (Millipore) membranes and visualized according to the method of Ploug et al. *Anal. Biochem.* 181:33–39, (1989). Areas of PVDF membranes containing stained peptides were excised and submitted for N-terminal amino acid sequencing (Univ. Calif. Davis, Protein Structure Lab). The results of amino acid sequencing of 4 distinct peptides fragments of RPP is shown in FIG. 1.

Isolation of guayule stembark mRNA.

Guayule stembark (10 g) was cut into 1 cm pieces and homogenized in 2 vol of quanidine buffer (8M guanidine HCL, 20 mM MES pH 7, 20 mM EDTA, 50 mM mercaptoethanol) in a polytron for 2 minutes. The homogenate was extracted with 1 vol of phenol:chloroform and centrifuged for 45 minutes at 10,000 rpm (Sorval SS-34 rotor) at 15 C. The aqueous phase was transferred to a fresh tube and centrifuged for 10 min at 10,000 rpm at 15 C. and the supernatant transferred to fresh tube. To this 0.7 vol of pre-cooled 100% ethanol and 0.2 vol of 1M acetic acid was added. The sample was placed in −20 C. overnight. The RNA was recovered by centrifugation for 10 min at 5,000 rpm at 4 C. The pellet was washed with sterile 3M sodium acetate (pH 5.2) at room temperature and centrifuged for 5 min at 10,000 rpm. The pellet was washed with 70% ethanol, vacuum dried and dissolved in sterile water. Poly-A+ mRNA was purified from RNA by fractionation on oligo-dT cellulose according to methods described in Sambrook et al. *Molecular Cloning, A Laboratory Manual*, 2nd Ed. 7.26–7.29 (1989).

Construction of guayule stembark cDNA libraries.

Guayule stembark mRNA was used to generate cDNA for construction of libraries in lambda ZAP, available in kit form from Strategene Inc., according to the protocol outlined by the manufacturer. Lambda ZAP is described by Short et al, *Nucl., Acids Res.* 16:7583–7600 (1988).

PCR amplification of guayule RPP cDNA

The guayule stembark cDNA libraries were initially screened with the 92 bp probe, sequence P5/6 (FIG. 2) generated by PCR amplification of guayule cDNA. The first strand cDNA synthesis was performed by using the Strategene, cDNA synthesis kit and following the manufacturer's instructions. About 1.5 µg of guayule stembark mRNA was incubated at 37 C. for 1 h in the presence of oligo-dT, reverse transcriptase and a mixture of nucleotides. The single stranded cDNA was precipitated by adding ammonium acetate (pH 4.5) to a final concentration of 0.5M followed by 2 vols of ethanol. The mixture was centrifuged in a microcentrifuge at 14,000 rpm at room temperature for 10 min and the pellet was washed with 200 µl of 70% ethanol, dried under vacuum and redissolved in 50 µl of sterile water.

Sequence P5 (FIG. 2), a degenerate, 20-mer oligonucleotide primer corresponding to a sense strand DNA of CNBr fragment #3 and sequence P6 (FIG. 2), a degenerate, 20-mer oligonucleotide primer corresponding to an antisense strand DNA of CNBr fragment #3 (FIG. 1) were used to generate the 92 bp P5/6 sequence (FIG. 2). A 20 µl PCR reaction mixture containing 100 pmol of each primer, 1 µl of the cDNA mixture described above, 0.2 mM of each nucleotide and 0.5 µl REPLINASE (DuPont) in 50 mM Tris-HCl buffer (pH 9.0) containing 20 mM ammonium sulfate and 1.5 mM magnesium chloride was amplified under a thermocycling regime of 94 C. for 1 min, 55 C. for 2 min and 72 C. for 3 min for 39 cycles followed by 10 min at 72 C. The resulting mixture was run on an agarose gel to reveal a 92 bp fragment. DNA sequence analysis of the fragment revealed an exact match to the amino acid sequence of CNBr fragment #3 as shown in FIGS. 2 and 3.

Subsequent to this, radioactively labeled $^{32}$P probes of P5/6 were regenerated by the PCR reaction, using 50 pmol of each primer P5 and P6 and utilizing the purified P5/6 probe as the template DNA. This resulted in high specific activity probe which was used to screen the lambda ZAP cDNA library, according to the methods outlined in Sambrook, et al. (op cit).

Subsequent to determining the sequence of the pRPP30 clone it was discovered that P5/6 encodes a 3' terminal region of the RPP gene (FIG. 3). Thus, when screening the cDNA library with P5/6 it resulted in the preferential isolation of only partial cDNA clones less than 900 bp in length. A few of these partial cDNA's were used, in turn, to isolate the full-length, pRPP30 cDNA clone (FIG. 3).

Screening of cDNA libraries

Plaques containing recombinant lambda ZAP cDNA's were transferred to membrane filters (Colony/Plaque Screen, DuPont) and subjected to an initial screening by hybridization to radio-actively labeled P5/6 in 6× SSPC, 5× Denhardt's solution, 50% formamide, 0.5% SDS, 200 µg/ml salmon sperm DNA, and 10% dextran sulfate for 18 h at 42 C. Washes were for 2 times at 10 min in 2× SSC followed by 2 times at 20 min in 2× SSC plus 0.1% SDS. Positive plaques from the initial screen were rescreened on nitrocellulose (Schleicher and Schuell) by hybridization to radioactively labeled P5/6 in 6× SSPE, 5× Denhardt's solution, 0.5% SDS and 100 µg/ml salmon sperm DNA for 18 h at 42 C. and washed the same as for the initial screens.

Clones which yielded positive responses to the second screen were then subjected to excision and circularization according to the lambda ZAP protocol. Phagemid DNA was isolated by standard miniprep procedures and separated on agarose gels. Those colonies resulting in Bluescript phagemid containing the largest cDNA inserts were further characterized by DNA sequencing.

DNA sequencing

DNA sequencing employed the dideoxy chain termination technique, utilizing SEQUENASE (U.S. Biochemical Corp) according to manufacturer's instructions.

The cleavage of RPP by CNBr resulted in four distinct peptide fragments which could be sequenced from their N-termini (FIG. 1). Amino acid sequences ranged from 17 to 36 residues in length. Of those, peptide fragments #3, #4, and #2 resulted in deduced DNA stretches of at least 17 bp with low degeneracy (FIG. 2). Oligonucleotides corresponding to those portions were synthesized and used to generate larger guayule cDNA fragments by PCR amplification. Of those, two successful PCR products were made. A 92 bp sequence, P5/6 which matched with the known CNBr fragment #3 (FIG. 2) and a 434 bp sequence, between primers P1 and P9 (FIG. 3) which contained regions of the RPP gene bridging CNBr fragments #4 and #2. Sequence P5/6 was used as a probe to successfully isolate a large cDNA clone designated c17 which contained an 823 bp insert coding for the 3' end of the RPP gene (not shown).

Full-length cDNA clones were isolated by screening against both the 92 bp probe and the 434 bp probe. Analysis of the full-length pRPP30 reveals an open reading frame (FIG. 3.) which contains 8 methionines at positions 1, 44, 56, 97, 129, 252, 327 and 371, and 2 cysteines, at positions 274 and 426. The pRPP30 polypeptide also contains 3 possible N-linked glycosylation sites at positions 132, 318 and 354. This is consistent with the structure of guayule RPP which is known to be a glycoprotein. The pRPP30 coding region is negatively charged with a deduced pKa of 6.15 which agrees with the experimentally derived value of 6.2. The pRPP30 clone contains a TGA stop codon and a 3' noncoding sequence of 250 bp which is AT-rich as expected for a termination sequence. The 5' noncoding region contains 23 bp and a consensus plant gene translation start site.

A computer search of GENBANK/EMBL and SWIS-SPROT using the BLAST algorithm showed homology to small dispersed regions of several cytochrome P450 with amino acid sequences of the 473 amino acid pRPP30 open reading frame. Later it was discovered that the RPP protein sequence showed considerable homology to the flaxseed AOS sequence (Song et al. op cit. (1993)).

Analyses of RPP as a Cytochrome P450

To verify that RPP had properties of an AOS-type cytochrome P450 it was subjected to spectral and biochemical analyses according to Song and Brash, op cit. (1991) and Zimmerman, op cit. (1966); Zimmerman and Vick, op cit. (1970) and Zimmerman and Feng, op cit. (1978).

Biochemical Analysis of Prenyltransferase Activity

Washed rubber particles were prepared by centrifugation according to Cornish and Backhaus, op cit.(1990) from a crude homogenate of guayule stembark. RPP was solubilized by sonicating washed particles in 0.5% CHAPS and passing that solution through a Millipore, Millex-GV, 0.22 μm, SLGV filter which removed all of the remaining rubber particles. Prenyltransferase activity was determined for each purification step by measuring the incorporation of $^{14}C$-isopentenyl pyrophosphate into isoprenoid derivatives according to Dogbo and Camara, op cit. (1987) and Kuntz et al. op cit. (1992) using dimethylallyl pyrophosphate (DMAPP) as the initiator to measure activity in 100 μl aliquots of protein extract Construction of the pBIRPP Binary Vector One means of using this invention is to insert the RPP coding region into the pBI121 binary plasmid vector (Jefferson R. A. et al. EMBO J. 6: 3901–3907 (1986)) downstream of the 35S promoter. This recombinant plasmid is transferred to Agrobacterium tumefaciens strain LBA 4404 where it is used to inoculate one of numerous plant species, such as tobacco, sunflower or guayule. The RPP coding region containing the 35S promoter is then incorporated into the plant's chromosomal DNA and the plant is replicated. The resulting transformed plant then produces large quantities of RPP which, in turn, leads to rubber biosynthesis in its cells. Rubber synthesis occurs because the substrates (IPP, DMAPP, FPP and Mg, etc.) are present within all plants. The rubber so made is then harvested from the plant tissues.

Figure 7:
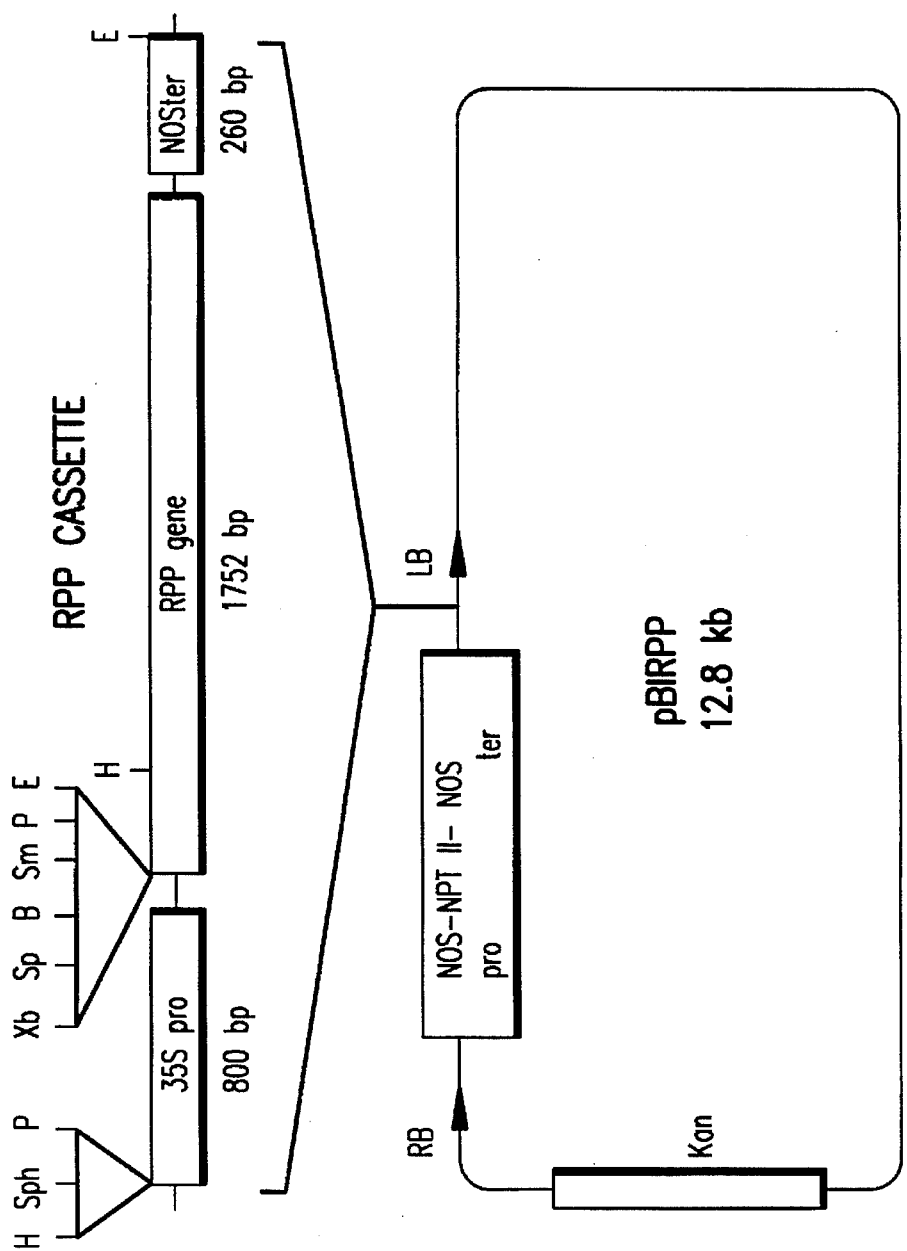
FIG. 7 displays a map of pBIRPP, the 12.8 kb, binary plasmid vector which is used to transform tobacco. It contains the RPP cassette in a sense orientation. RPP cDNA from pRPP30 was inserted downstream of the 35S promoter and upstream of the NOS terminator, by replacing the GUS gene from pBI121.
Figure 8A:
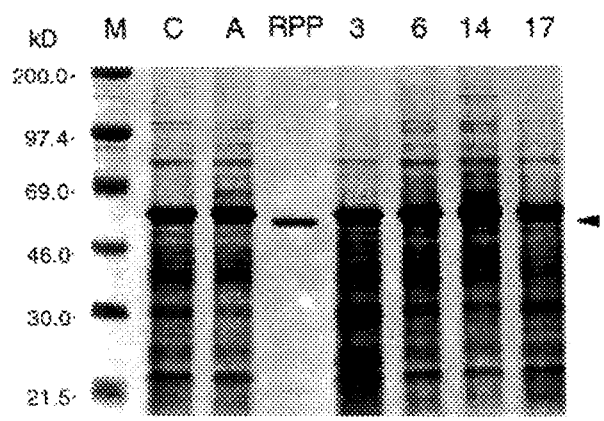
FIG. 8A shows a coomassie blue stained, SDS gel of total proteins extracted from tobacco transformed with RPP expressed in the sense orientation. It shows RPP (arrow) in 4 different transformants (#3, #6, #14, and #17). Proteins from non-transformed, control tobacco (C) and from tobacco with an antisense construct of RPP cDNA (A) do not produce RPP. Molecular weight markers (M) and the position of authentic from RPP in washed guayule rubber particles (RPP) are indicated.
Figure 8B:
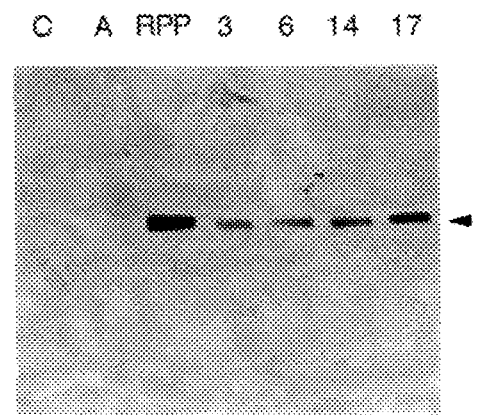
FIG. 8B shows a Western hybridization of a gel identical to Panel A. The blot was probed with a monospecific RPP-antibody and stained with alkaline phosphatase conjugated, secondary antibody. The blot shows a single band (arrow) of RPP in each of the tobacco transformants (#3, #6, #14, #17) in the sense orientation. Control tobacco (C) and antisense constructs (A) do not produce RPP.
Figure 8D:
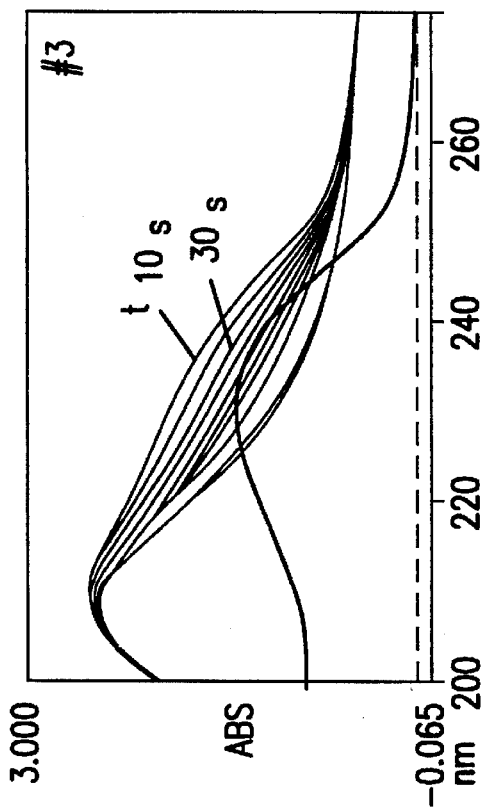
FIG. 8D shows high AOS activity in protein prepared from tobacco transformant #3. These plants express the foreign guayule RPP gene and produce functional RPP. This is observed by the rapid disappearance of the 234 nm LOOH peak scanned at 10 sec intervals after following addition of tobacco protein extracts. Scans after 10 and 30 seconds, respectively, are indicated by arrows and are labeled. Repetitive scans over several minutes show the complete loss of LOOH in the sample cuvette after 10 minutes.
Figure 8C:
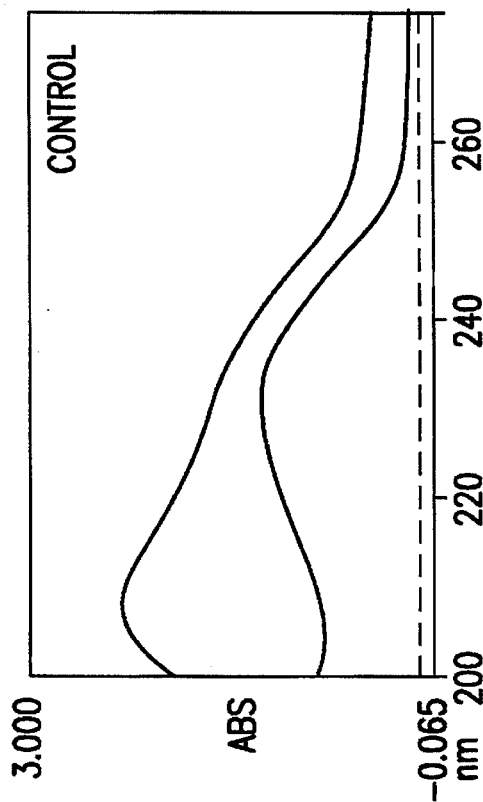
FIG. 8C shows that AOS-like activity of functional RPP is absent in protein extracts from non-transformed, control tobacco (C). These plants do not produce RPP and consequently do not metabolize LOOH. The spectra depicts repetitive scans made at 10 sec intervals over several minutes with no loss of LOOH in the sample cuvette.
Figure 9A:
FIG. 9 displays electron micrographs of non-transformed (FIG. 9A) and pBIRPP-transformed (FIGS. 9B and C) tobacco (transformant #3) that produces functional guayule RPP. Cells from non-transformed plants (FIG. 9A) do not contain rubber particles, whereas cells from transformed plants (in FIGS. 9B and C) do contain rubber particles (arrows) which are observed primarily in the vacuoles. Bar equals 2 um.
Figure 9B:
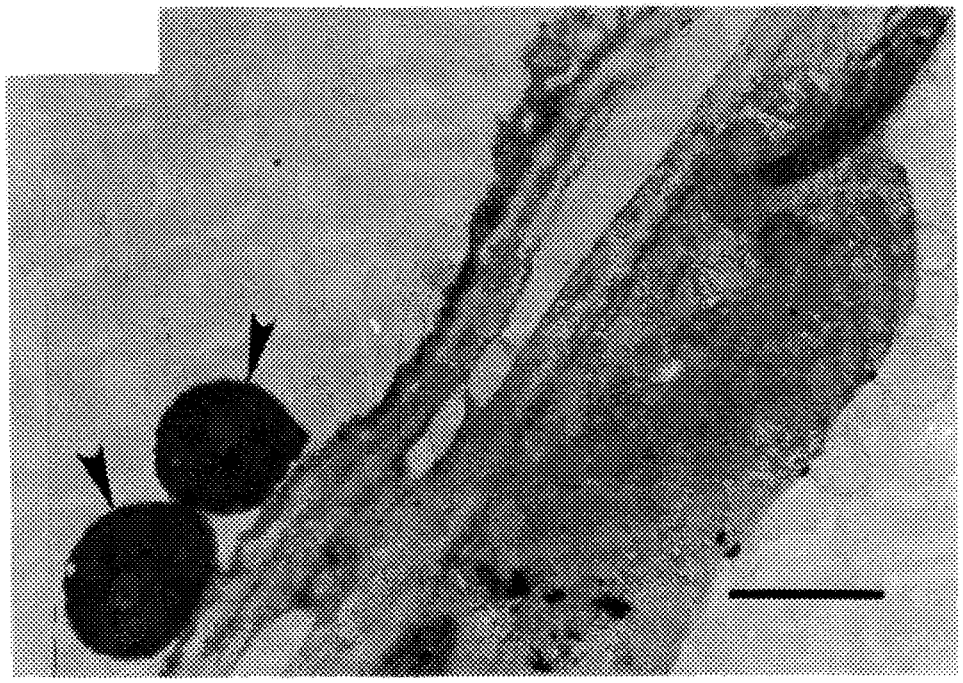
Figure 9C:
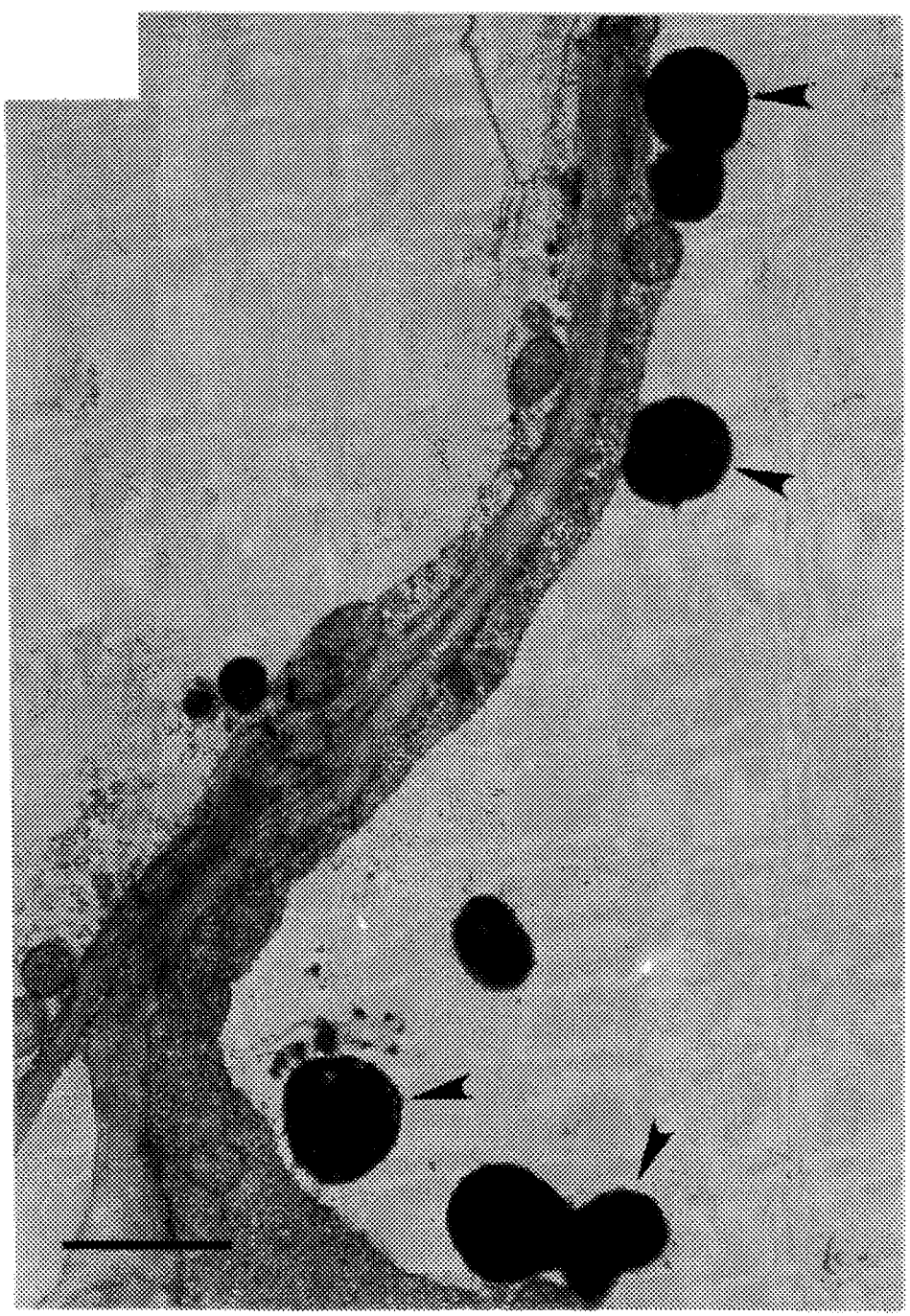
Figure 10A:
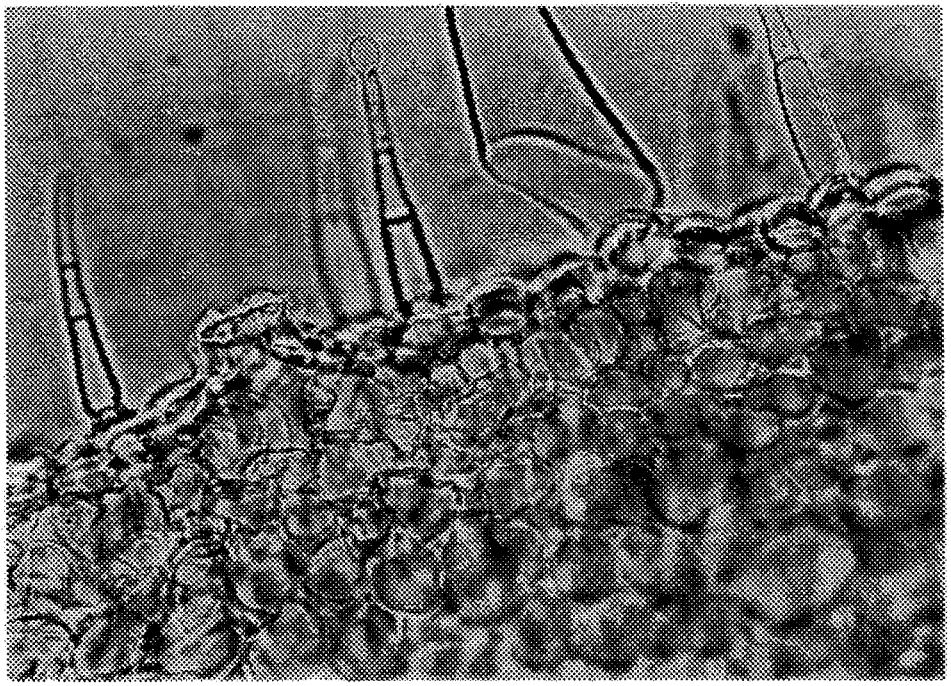
FIG. 10 displays light micrographs of non-transformed (FIG. 10A) and pBIRPP transformed (FIG. 10B) tobacco plants stained with calco oil blue which is specific for rubber. Cells of non-transformed plants do not contain rubber, whereas cells of transformed plants contain rubber which appears as dark blue staining globules within the cells (arrows).
Figure 10B:
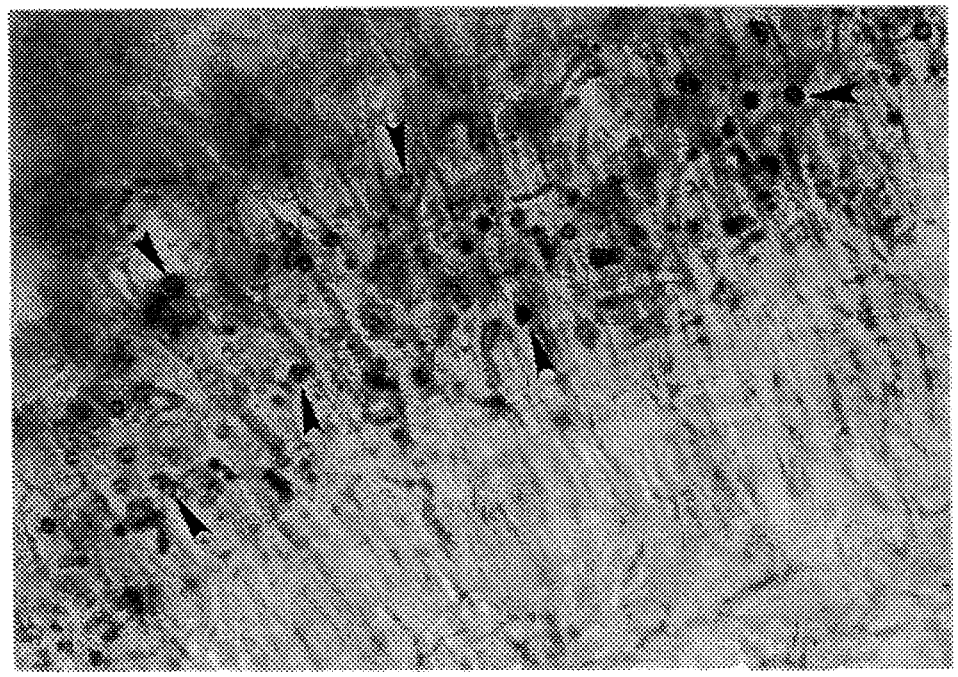

Tobacco transformation was performed using a binary vector derived from pBI121 in which the GUS gene was replaced with RPP downstream of the strong CaMV 35S promoter. This new vector was constructed by first digesting pBI121 with SmaI and SstI to remove the 1.9 kb GUS insert and filling in the SstI site with T4 Polymerase. The resulting linear 10 kb fragment was gel purified and circularized by blunt end ligation. This gave a circular GUS⁻ minus pBI121. This was then cut with BamHI, filled in with Klenow and cut again with XbaI. The linear fragment containing one sticky XbaI end and another filled in BamHI blunt end was gel purified. Concurrently, the pRPP30 insert in the SK⁻ vector was digested with XhoI and filled in with Klenow. This linearized plasmid was then digested with XbaI to give an RPP fragment with one sticky XbaI site at the 5' end of RPP and a blunt 3' end. This was ligated to the complementary GUS⁻ minus fragment to yield a 12.8 kb, pBIRRP binary plasmid vector containing the RPP gene in a sense orientation downstream of the CaMV 35S promoter (FIG. 7). Tobacco plants are transformed by the leaf disk method (Horsch et al. Science, 227:1229–1231 (1985)) selected, and grown to maturity.

Microscopic Analysis of Transformed Tobacco

Transgenic tobacco plants were analyzed by light microscopy following the staining of tissue sections by the method of Addicott, op cit. (1944) or by electron microscopy according to the method of Backhaus and Walsh, op cit. (1983)

Other Uses of this Invention

Another means of utilizing this invention is to insert the RPP coding region into the pYEDP60 plasmid vector (Truan et al. Gene 125: 49–55 (1993)) downstream of the GAL 10 promoter. The plasmid is then transferred to yeast and allowed to grow for a period and before it is induced with galactose to produce high levels of RPP. Yeast can be selected which are compatible with eukaryotic cytochrome P450s (Urban et al. Biochimie 72:463–472 (1990)). Rubber biosynthesis results because the substrates of IPP and FPP are synthesized by yeast. The rubber, so made, is then harvested from the cells.

Another means of utilizing this invention is to insert the RPP coding region into the pET3 plasmid vector (Sturdier, et al. Methods in Enzymol. 185:60–98 (1990)) downstream of the T7 promoter. The plasmid is then transferred to E. coli strain BL21 and allowed to grow for a period of several hours and then is induced to produce T7 polymerase which causes high levels of RPP to be produced. Rubber biosynthesis results when the substrates IPP and FPP are provided in the medium. The rubber, so made, is then harvested from the cells.

The cDNA molecules of this invention can be operatively linked to expression control sequences and used in various eukaryotic or prokaryotic host cells to produce RPP. The cDNA sequences of this invention, are also useful as probes to screen cDNA or genomic DNA from other sources capable of rubber biosynthesis. These genomic sequences, like the above cDNA sequences of this invention, would also be useful for isolating RPP genes from other organisms.

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. An isolated nucleic acid molecule encoding a guayule rubber particle protein.

2. The nucleic acid molecule of claim 1 which encodes a guayule rubber particle protein having an amino acid sequence as depicted in FIG. 3. (Sequence ID No. 12).

3. The nucleic acid molecule of claim 2, having a nucleic acid sequence as depicted in FIG. 3 (Sequence ID No. 12).

4. A vector comprising the nucleic acid molecule of claim 1.

5. A vector comprising the nucleic acid molecule of claim 2.

6. A vector comprising the nucleic acid molecule of claim 3.

7. The vector of claim 4, wherein the nucleic acid encoding the guayule rubber particle protein is operatively linked to a promoter element.

8. The vector of claim 5, wherein the nucleic acid encoding the guayule rubber particle protein is operatively linked to a promoter element.

9. The vector of claim 6, wherein the nucleic acid encoding the guayule rubber particle protein is operatively linked to a promoter element.

10. The vector of claim 7 wherein said promoter element is selected from the group consisting of a lacZ promoter, a trp promoter, a trc promoter, a tac promoter, a T7 polymerase promoter, a GAL 1 promoter, a GAL 10 promoter, a NOS promoter and a cauliflower mosaic virus 35S promoter.

11. The vector of claim 8 wherein said promoter element is selected from the group consisting of a lacZ promoter, a trp promoter, a trc promoter, a tac promoter, a T7 polymerase promoter, a GAL 1 promoter, a GAL 10 promoter, a NOS promoter and a cauliflower mosaic virus 35S promoter.

12. The vector of claim 9 wherein said promoter element is selected from the group consisting of a lacZ promoter, a trp promoter, a trc promoter, a tac promoter, a T7 polymerase promoter, a GAL 1 promoter, a GAL 10 promoter, a NOS promoter and a cauliflower mosaic virus 35S promoter.

13. An isolated nucleic acid molecule which hybridizes to the nucleic acid molecule of claim 1 under conditions represented by a wash stringency of 0.45M NaCl, 0.04M sodium citrate, 0.1% sodium dodecyl sulfate at 45° C.

14. An isolated nucleic acid molecule which hybridizes to the nucleic acid molecule of claim 2 under conditions represented by a wash stringency of 0.45M NaCl, 0.04M sodium citrate, 0.1% sodium dodecyl sulfate at 45° C.

15. An isolated nucleic acid molecule which hybridizes to the nucleic acid molecule of claim 3 under conditions represented by a wash stringency of 0.45M NaCl, 0.04M sodium citrate, 0.1% sodium dodecyl sulfate at 45° C.

16. A transgenic plant containing, as a transgene, the nucleic acid of claim 1.

17. A transgenic plant containing, as a transgene, the nucleic acid of claim 2.

18. A transgenic plant containing, as a transgene, the nucleic acid of claim 3.

19. A plant host cell containing the vector of claim 4.

20. A plant host cell containing the vector of claim 5.

21. A plant host cell containing the vector of claim 6.

* * * * *

UNITED STATES PATENT AND TRADEMARK OFFICE
CERTIFICATE OF CORRECTION

PATENT NO. : 5,633,433
DATED : May 27, 1997
INVENTOR(S) : Ralph A. Backhaus; Zhiqiang Pan It is certified that error appears in the above-indentified patent and that said Letters Patent is hereby corrected as shown below:

Col. 1, line 55, "(RUT)" should read --(RuT)--;
Col. 4, line 53, "Polymers" should read --polymers--;
Col. 5, line 23, "Polymerase" should read --polymerase--;
Col. 6, line 23, "Sci." should read --Acad. Sci.--;
Col. 12, line 26, "Baoteriophage" should read --Bacteriophage--and,
Col. 16, line 21, "Polymerase" should read --polymerase--.

Signed and Sealed this

Eighteenth Day of November 1997

Attest:

BRUCE LEHMAN

*Attesting Officer*          *Commissioner of Patents and Trademarks*

UNITED STATES PATENT AND TRADEMARK OFFICE
CERTIFICATE OF CORRECTION

| | | |
|---|---|---|
| PATENT NO. | : 5,633,433 | |
| APPLICATION NO. | : 08/240012 | |
| DATED | : May 27, 1997 | |
| INVENTOR(S) | : Ralph A. Backhaus and Zhiqiang Pan | |

It is certified that error appears in the above-identified patent and that said Letters Patent is hereby corrected as shown below:

Col. 1, lines 11-12, "CSRS-90-38200-55668" should read --CSRS-90-38200-5568--

Signed and Sealed this

Eleventh Day of January, 2011

David J. Kappos
*Director of the United States Patent and Trademark Office*